United States Patent
Cohen et al.

(10) Patent No.: US 9,993,497 B2
(45) Date of Patent: *Jun. 12, 2018

(54) USE OF ALGINATE COMPOSITIONS IN PREVENTING OR REDUCING LIVER DAMAGE CAUSED BY A HEPATOTOXIC AGENT

(71) Applicants: HADASIT MEDICAL RESEARCH SERVICES AND DEVELOPMENT LTD., Jerusalem (IL); B.G. NEGEV TECHNOLOGIES & APPLICATIONS LTD., Beer-Sheva (IL)

(72) Inventors: Smadar Cohen, Beer-Sheva (IL); Yaron Ilan, Kfar-Tavor (IL); Eyal Shteyer, Mevaseret Zion (IL); Ami Ben-Ya'acov, Jerusalem (IL)

(73) Assignees: Hadasit Medical Research Services and Development Ltd., Jerusalem (IL); B.G. Negev Technologies & Applications Ltd., at Ben-Gurion University, Beer-Sheva (IL)

( * ) Notice: Subject to any disclaimer, the term of this patent is extended or adjusted under 35 U.S.C. 154(b) by 63 days.

This patent is subject to a terminal disclaimer.

(21) Appl. No.: 14/758,603

(22) PCT Filed: Dec. 30, 2013

(86) PCT No.: PCT/IL2013/051088
§ 371 (c)(1),
(2) Date: Jun. 30, 2015

(87) PCT Pub. No.: WO2014/102801
PCT Pub. Date: Jul. 3, 2014

(65) Prior Publication Data
US 2015/0352144 A1    Dec. 10, 2015

Related U.S. Application Data

(60) Provisional application No. 61/747,325, filed on Dec. 30, 2012, provisional application No. 61/747,328, filed on Dec. 30, 2012.

(51) Int. Cl.
| | | |
|---|---|---|
| *A61K 31/734* | (2006.01) | |
| *A61K 31/167* | (2006.01) | |
| *A61K 9/00* | (2006.01) | |
| *A61K 45/06* | (2006.01) | |

(52) U.S. Cl.
CPC .......... *A61K 31/734* (2013.01); *A61K 9/0053* (2013.01); *A61K 31/167* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,405,861 A | 8/1946 | Tod | |
| 5,384,400 A | 1/1995 | Crescenzi et al. | |
| 5,888,987 A | 3/1999 | Haynes et al. | |
| 5,955,107 A * | 9/1999 | Augello | A61K 9/0056 424/441 |
| 6,425,918 B1 | 7/2002 | Shapiro et al. | |
| 2005/0226968 A1* | 10/2005 | Holzschuh | A22C 13/0013 426/138 |
| 2006/0083721 A1 | 4/2006 | Cohen et al. | |
| 2015/0335675 A1 | 11/2015 | Cohen et al. | |

FOREIGN PATENT DOCUMENTS

| | | |
|---|---|---|
| DE | 19723155 | 12/1998 |
| EP | 1842544 | 10/2007 |
| GB | 555940 | 9/1943 |
| IN | 1248MUM/2010 | 2/2013 |
| JP | 10-114683 | 5/1998 |
| KR | 10-2010-0008683 | 1/2010 |
| RU | 2019981 | 9/1994 |
| WO | WO 95/19743 | 7/1995 |
| WO | WO 97/44070 | 11/1997 |
| WO | WO 98/12228 | 3/1998 |
| WO | WO 03/037299 | 5/2003 |
| WO | WO 2004/082594 | 9/2004 |
| WO | WO 2004/098668 | 11/2004 |

(Continued)

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002.*
Chang, C. Y., & Schiano, T. D. (2007). Review article: drug hepatotoxicity. Alimentary pharmacology & therapeutics, 25(10), 1135-1151.*
Wilkinson, G. Pharmacokinetics, The Dynamics of Drug Absorption, Distribution, and Elimination (2001). In: Goodman and Gilman's the pharmacological basis of therapeutics. International edition, 10th edition, McGrow Hill, 971.*
Supplementary European Search Report and the European Search Opinion dated Jul. 12, 2016 From the European Patent Office Re. Application No. 13869473.2.
Supplementary European Search Report and the European Search Opinion dated Jun. 27, 2016 From the European Patent Office Re. Application No. 13869503.6.

(Continued)

*Primary Examiner* — Shaojia A Jiang
*Assistant Examiner* — Dale R Miller

(57) ABSTRACT

Disclosed herein are compositions, methods and uses utilizing alginate compositions, for treating, preventing and/or reducing liver damage induced by a hepatotoxic agent, and for treating a medical condition treatable by a hepatotoxic agent, in which an alginate composition is administered prior to, concomitant with, or shortly after exposure to a hepatotoxic agent. Also disclosed are pharmaceutical compositions comprising a hepatotoxic agent and an alginate composition and uses thereof for treating medical conditions treatable by the hepatotoxic agent.

27 Claims, 8 Drawing Sheets
(5 of 8 Drawing Sheet(s) Filed in Color)

(56) References Cited

FOREIGN PATENT DOCUMENTS

| WO | WO 2007/113454 | 10/2007 |
|---|---|---|
| WO | WO 2009/069131 | 6/2009 |
| WO | WO 2009/083759 | 7/2009 |
| WO | WO 2010/104464 | 9/2010 |
| WO | WO 2014/102801 | 7/2014 |
| WO | WO 2014/102802 | 7/2014 |

OTHER PUBLICATIONS

Aoki et al. "Diffusion Coefficients in Viscous Sodium Alginate Solutions", Electrochimica Acta, XP028945079, 83: 348-353, Available Online Aug. 10, 2012. Described Alginate Compositions and Their Properties.
FAO "Compendium of Food Additive Specifications: Sodium Alginate", FAO, Food and Agriculture Organisation, 49th JEFCA, XP055280173, pp. 1-3, Jan. 1, 1997. Process in Section 'Microbiological Citeria': Sodium Alginate Prepared by Dispersing Alginate Sodium in Saline Solution and Homogenizing at High Speed, Descripted Alginate Compositions and Their Properties.
Aoki et al. "Diffusion Coefficients in Viscous Sodium Alginate Solutions", Department of Applied Physics, University of Fukui, Japan, p. 1-23, Aug. 10, 2012.
Nagarwal et al. "Chitosan Coated Sodium Alginate-Chitosan Nanoparticles Loaded With 5-FU for Ocular Delivery: In Vitro Characterization and In Vivo Study in Rabbit Eye", European Journal of Pharmaceutical Sciences, XP002758840, 47(4): 678-685, Available Online Aug. 16, 2012. Pharmaceutical Compositions Comprising Sodium Alginate (Which Is Also a Carrier) and 5FU (Which Is an Hepatotoxic Agent).
International Preliminary Report on Patentability dated Jul. 9, 2015 From the International Bureau of WIPO Re. Application No. PCT/IL2013/051088.
International Preliminary Report on Patentability dated Jul. 9, 2015 From the International Bureau of WIPO Re. Application No. PCT/IL2013/051089.
International Search Report and the Written Opinion dated Apr. 1, 2014 From the International Searching Authority Re. Application No. PCT/IL2013/051089.
International Search Report and the Written Opinion dated Apr. 9, 2014 From the International Searching Authority Re. Application No. PCT/IL2013/051088.
Balkrishnan et al. "Self-Cross-Linking Biopolymers as Injectable In Situ Forming Biodegradable Scaffolds", Biomaterials, 26: 3941-3951, 2005.
De Abajo et al. "Acute and Clinically Relevant Drug-Induced Liver Injury: A Population Based Case-Control Study", British Journal of Clinical Pharmacology, 58(1): 71-80, 2004.
Dvir-Ginzberg et al. "Liver Tissue Engineering Within Alginate Scaffolds: Effects of Cell-Seeding Density on Hepacyte Viability, Morphology, and Function", Tissue Engineering, 9(4): 757-766, 2003.
Earle et al. "Hepatectomy Enables Prolonged Survival in Select Patients With Isolated Noncolorectal Liver Metastasis", Journal of the American College of Surgeons, 203: 436-446, 2006.
Geller et al. "Outcome of 1000 Liver Cancer Patients Evaluated at the UPMC Liver Cancer Center", Presented at the 2005 American Hepato-Pancreato-Biliary Association Congress, Hollywood, Florida, USA, Apr. 14-17, 2005, 2005 AHPBA Annual Meeting, Journal of Gastrointestinal Surgery, 10(1): 63-68, Jan. 2006.
Ichi et al. "Increase of Ceramide in the Liver and Plasma After Carbon Tetrachloride Intoxication in the Rat". Journal of Nutritional Science and Vitaminology, 53(1): 53-56, Feb. 2007.
Kaplowitz "Drug-Induced Liver Injury", Clinical Infectious Diseases, CID, 38(Suppl.2): S44-S48, 2004.
Khotimchenko et al. "Healing and Preventive Effects of Calcium Alginate on Carbon Tetrachloride Induced Liver Injury in Rats", Marine Drugs, 2: 108-122, 2004. Abstract, p. 113, 115-116.

Kubota et al. "Measurement of Liver Volume and Hepatic Functional Reserve as a Guide to Decision-Making in Resectional Surgery for Hepatic Tumors", Hepatology, 26: 1176-1181, 1997.
Landa et al. "Effect of Injectable Alginate Implant on Cardiac Remodeling and Function After Recent and Old Infarcts in Rat", Circulation, 117: 1388-1396, Mar. 3, 2008.
Madoff et al. "Portal Vein Embolization in Preparation for Major Hepatic Resection: Evolution of a New Standard of Care", Journal of Vascular and Interventional Radiology, 16(6): 779-790, Jun. 2005.
Maruyama et al. "Duration of Liver Ischemia and Hepatic Regeneration After Hepatectomy in Rats", Journal of Surgical Research, 58: 290-294, 1995.
Mirshafiey et al. "Sodium Alginate as a Novel Therapeutic Option in Experimental Colitis", Scandinavian Journal of Immunology, 61: 316-321, 2005.
Razavi et al. Therapeutic Effect of Sodium Alginate in Experimental Chronic Ulcerative Colitis, Iranian Journal of Allergy, Asthma and Immunology, 7(1): Mar. 13-18, 2008.
Seifert et al. "Production of Small, Monodispersed Alginate Beads for Cell Immobilization", Biotechnology Progress, 13: 582-568, 1997.
Tajiri et al. "Practical Guidelines for Diagnosis and Early Management of Drug Induced Liver Injury", World Journal of Gastroenterology, 14(44): 6774-6785, Nov. 28, 2008.
Tsur-Gang et al. "The Effects of Peptide-Based Modification of Alginate on Left Ventricular Remodeling and Function After Myocardial Infarction", Biomaterials, 30: 189-195, 2009.
Official Action dated Dec. 22, 2016 from the US Patent and Trademark Office Re. U.S. Appl. No. 14/758,589. (34 pages).
Advisory Action Before the Filing of an Appeal Brief dated Nov. 13, 2017 from the US Patent and Trademark Office Re. U.S. Appl. No. 14/758,589. (7 pages).
Applicant-Initiated Interview Summary dated Dec. 12, 2017 from the US Patent and Trademark Office Re. U.S. Appl. No. 14/758,589. (4 pages).
Applicant-Initiated Interview Summary dated Dec. 19, 2017 from the US Patent and Trademark Office Re. U.S. Appl. No. 14/758,589. (3 pages).
Communication Pursuant to Article 94(3) EPC dated Jun. 14, 2017 from the European Patent Office Re. Application No. 13869503.6. (6 Pages).
Communication Pursuant to Article 94(3) EPC dated Jun. 19, 2017 from the European Patent Office Re. Application No. 13869473.2. (7 Pages).
Official Action dated Aug. 17, 2017 from the US Patent and Trademark Office Re. U.S. Appl. No. 14/758,589. (23 pages).
ProNova "ProNova VLVG Sodium Alginate Description" Retrieved from novamatrix.biz/store, 3 Pages, Aug. 23, 2017.
Office Action dated Nov. 27, 2017 From the Israel Patent Office Re. Application No. 239705 and Its Translation Into English. (9 Pages).
Office Action dated Nov. 27, 2017 from the Israel Patent Office Re. Application No. 239706 and Its Translation Into English. (11 Pages).
Communication Pursuant to Article 94(3) EPC dated Mar. 13, 2018 from the European Patent Office Re. Application No. 13869473.2. (5 Pages).
Communication Pursuant to Article 94(3) EPC dated Mar. 20, 2018 From the European Patent Office Re. Application No. 13869503.6. (6 Pages).
Liu et al. "[Pharmacokinetics of Doxorubicin Alginate Microspheres and Evaluation of Its Hepatic Arterial Embolization In Vivo]", Yao Xue Xue Bao = Acta Pharmaceutica Sinica, 41(8): 778-783, Aug. 2006. Abstract.
Remel "Phosphate Buffer (Butterfield's Buffer)", Remel, XP055457533, Retrieved From the Internet, Product Description, 1 P., Jun. 10, 2010.
Villay et al. "Comparison of Polysccharide Degradations by Dynamic High-Pressue Homogenization", Food Hydrocolloids, XP028352071, 27(2): 278-286, Jun. 2012.

* cited by examiner

USE OF ALGINATE COMPOSITIONS IN PREVENTING OR REDUCING LIVER DAMAGE CAUSED BY A HEPATOTOXIC AGENT

RELATED APPLICATIONS

This application is a National Phase of PCT Patent Application No. PCT/IL2013/051088 having International filing date of Dec. 30, 2013, which claims the benefit of priority under 35 USC § 119(e) of U.S. Provisional Patent Application Nos. 61/747,325 filed on Dec. 30, 2012 and 61/747,328 filed on Dec. 30, 2012. The contents of the above applications are all incorporated by reference as if fully set forth herein in their entirety.

FIELD AND BACKGROUND OF THE INVENTION

The present invention, in some embodiments thereof, relates to a therapy and, more particularly, but not exclusively, to novel therapeutic methodologies for reducing or preventing liver damage by utilizing alginate-based compositions.

Alginate is an anionic polysaccharide derived from brown algae. Alginate is a to linear block co-polymer of (1-4)-linked β-D-mannuronic acid (M) and α-L-guluronic acid (G). The monomers can appear in homopolymeric blocks of consecutive G-residues (G-blocks), consecutive M-residues (M-blocks), or alternating M- and G-residues (MG-blocks).

Sodium alginate is soluble in water, and, in the presence of divalent cations, such as calcium ions, alginate forms a hydrogel. In nature, alginate exists in both the soluble form and as a hydrogel. The hydrogel protects brown algae from stress caused by the hydrostatic pressure of water and by waves.

The ratio of mannuronic acid to guluronic acid (M/G) in alginate differs according to the type of algae, and according to environmental conditions. The G residues in alginate have a particularly high affinity to calcium ions. Consequently, the amount of G and length of G-sequences influences the extent of alginate crosslinking and the mechanical properties of the formed hydrogel.

In addition to diversity in M/G ratio, alginate may vary in molecular weight. In nature, alginate usually has a molecular weight in a range of 100-200 kDa. Using different treatment protocols, such as heat and γ-radiation, the molecular weight of alginate can be reduced. Alginates with molecular weights of approximately 50 kDa are commercially available.

International Patent Application PCT/IL97/00191 (published as WO 97/44070) describes implantable polysaccharide (e.g. alginate) sponges for use as a matrix, substrate or scaffold for the cultivation of mammalian cells in vitro prior to their implantation to replace damaged or removed tissue.

International Patent Application PCT/IL2004/000371 (published as WO 2004/098669) describes injectable cross-linked alginate, which forms a hydrogel in vivo, for use in the repair of cardiac tissue damage and ablation of cardiac arrhythmias, when locally applied onto the cardiac tissue.

International Patent Application PCT/IL2008/001552 (published as WO 2009/069131) describes treatment of hepatic disorders via administration of cross-linked or non-cross-linked alginate biomaterial. Local administration to the liver of alginate in solid, hydrogel or liquid form is described, as well as systemic administration by injection of alginate in liquid form.

Landa, N. et al. [*Circulation* 117:1388-1396 (2008)] describes calcium-crosslinked alginate in an injectable low-viscosity solution, which can undergo phase transition into a hydrogel after injection. Injection of the alginate solution into a cardiac infarct was reported to prevent adverse cardiac remodeling and dysfunction.

Orally administered calcium alginate (403 kDa) has been reported to reduce liver damage caused by ingestion of $CCl_4$ for one week in mice [Khotimchenko & Khotimchenko, *Mar Drugs* 2:108-122 (2004)].

Tsur-Gang et al. [*Biomaterials* 30:189-195 (2009)] describes modification of alginate with the adhesion peptide RGD in order to cause alginate to better interdigitate with the host. RGD-modified alginate is also described in International Patent Application PCT/IL2004/000371 (published as WO 2009/069131).

Liver disease represents a worldwide health problem in humans, which can be managed pharmacologically in only a few cases. Development of new drugs depends primarily on the availability of suitable animal models. The pathophysiology of liver disease includes complex phenomena such as interrelationships on humoral basis, the highly sophisticated morphological organization of the organ itself, and the integrity of metabolic and immunologic pathways and their regulation in the individual cell types of the liver.

The liver is responsible for the synthesis of serum proteins; intermediary metabolism of amino acids, lipids, and carbohydrates; and detoxification of foreign compounds. These functions are usually seriously hampered in the various animal models of liver diseases.

More than 900 drugs have been implicated in causing liver injury [Friedman et al. (2003), *Current Diagnosis & Treatment in Gastroenterology*, New York: Lang Medical Books/McGraw-Hill. pp. 664-679]. Hepatotoxicity is the most common reason for a drug to be withdrawn from the market, and also accounts for a substantial number of compound failures during drug development. Drug-induced liver injury (DILI) is responsible for 5% of all hospital admissions and 50% of all acute liver failures. Liver function tests are routinely used to monitor subjects taking any of a variety of drugs (e.g., methotrexate, carbamazepine).

Paracetamol intoxication, which may be intentional or unintentional, is one of the major causes of death from drug overdose and may lead to acute liver failure, sometimes irreversibly. Paracetamol-induced liver toxicity is the most prevalent cause of acute liver failure in the Western world. Currently, an accepted treatment is N-acetylcysteine administration, which has several drawbacks, mainly due to its limited therapeutic window.

Knowledge of the mechanisms of paracetamol hepatotoxicity derives to a large extent from studies performed in mice treated with paracetamol. In mice, covalent binding of APAP metabolites to liver proteins begins within 15 minutes of the overdose, concurrently with the beginning of glutathione depletion, and peaks within 1-2 hours. This is followed by other pathogenetic events such as disturbance of intracellular calcium homeostasis, oxidative and nitrosative stress, massive hepatic congestion, and activation of the innate immunity including natural-killer and natural-killer cells with T-cell receptors, macrophages and neutrophils. Oncotic necrosis is the main mode of hepatocyte cell death.

Alcoholic liver disease is the major cause of liver disease in Western countries. Chronic consumption of alcohol results in the secretion of pro-inflammatory cytokines (TNF-α, IL-6 and IL-8), oxidative stress, lipid peroxidation, and acetaldehyde toxicity. These factors cause inflammation, apoptosis and eventually fibrosis of liver cells.

Additional art includes International Patent Application Publication WO 95/19743; International Patent Application Publication WO 98/12228; International Patent Application Publication WO 2004/082594; German Patent Application Publication DE 19723155 A1; Ichi et al. [*J Nutr Sci Vitaminol* 53:53-56 (2007)]; Seifert & Phillips [*Biotechnol Prog* 13:562-568 (1997)]; Balakrishnan & Jayakrishnan [Biomaterials 26:3941-3951 (2005)]; Maruyama et al. [*J Surg Res* 58:29-294 (1995)]; and Dvir-Ginzberg et al. [*Tissue Engineering* 9:757-766 (2003)].

SUMMARY OF THE INVENTION

As exemplified herein, systemically administered alginate is surprisingly effective at treating liver damage associated with chemical hepatotoxicity, when the alginate is administered prior to, concomitant with, or shortly after exposure to hepatotoxicity. Following such administration, liver damage may be reduced, nullified or even not induced, rendering administration of hepatotoxic agents without an alginate generally inadvisable. The high degree of biocompatibility of alginate renders alginate unusually suitable for being administered prior to, shortly after, or in combination with exposure to hepatotoxic agents, or for being co-formulated with a hepatotoxic agent.

According to an aspect of some embodiments of the invention, there is provided a method of reducing or preventing a liver damage caused by a hepatotoxic agent, the method comprising administering to a subject exposed to the hepatotoxic agent a therapeutically effective amount of an alginate composition, the administering being effected prior to, concomitant with, or shortly after exposure to the hepatotoxic agent, thereby reducing or preventing liver damage.

According to an aspect of some embodiments of the invention, there is provided a method of treating a medical condition treatable by a hepatotoxic agent in a subject in need thereof, the method comprising co-administering to the subject a therapeutically effective amount of the hepatotoxic agent and a therapeutically effective amount of an alginate composition, the co-administering being effected such that the alginate composition is administered to the subject during a time period ranging from 100 minutes prior to administration of the hepatotoxic agent to 50 minutes subsequent to administration of the hepatotoxic agent, thereby treating the medical condition.

According to an aspect of some embodiments of the invention, there is provided a method of treating a medical condition selected from the group consisting of the medical conditions listed in Table 1 (right column) herein in a subject in need thereof, the method comprising co-administering to the subject a therapeutically effective amount of a hepatotoxic agent selected from the group consisting of the hepatotoxic drugs listed in Table 1 (left column) herein, the aforementioned hepatotoxic drug being respective to the aforementioned condition, and a therapeutically effective amount of an alginate composition, the co-administering being effected such that the alginate composition is administered to the subject during a time period ranging from 100 minutes prior to administration of the hepatotoxic agent to 50 minutes subsequent to administration of the hepatotoxic agent, thereby treating the medical condition.

According to an aspect of some embodiments of the invention, there is provided a method of treating a liver damage induced by a hepatotoxic agent, the method comprising administering to a subject in need thereof a therapeutically effective amount of an alginate composition, the administering being effected prior to, concomitant with, or up to 50 minutes after administration of the hepatotoxic agent, thereby treating the liver injury.

According to an aspect of some embodiments of the invention, there is provided a use of an alginate composition in the manufacture of a medicament for reducing or preventing a liver damage caused by a hepatotoxic agent, the medicament being for administration prior to, concomitant with, or shortly after exposure to the hepatotoxic agent.

According to an aspect of some embodiments of the invention, there is provided a use of an alginate composition in the manufacture of a medicament for treating a medical condition treatable by a hepatotoxic agent, the treating comprising co-administering a therapeutically effective amount of the hepatotoxic agent and a therapeutically effective amount of the alginate composition, the co-administering being effected such that the alginate composition is administered to a subject during a time period ranging from 100 minutes prior to administration of the hepatotoxic agent to 50 minutes subsequent to administration of the hepatotoxic agent.

According to an aspect of some embodiments of the invention, there is provided a use of an alginate composition in the manufacture of a medicament for treating a medical condition selected from the group consisting of the medical conditions listed in Table 1 (right column) herein, the treating comprising co-administering a therapeutically effective amount of a hepatotoxic agent selected from the group consisting of the hepatotoxic drugs listed in Table 1 (left column) herein, the aforementioned hepatotoxic drug being respective to the aforementioned condition, and a therapeutically effective amount of the alginate composition, the co-administering being effected such that the alginate composition is administered to a subject during a time period ranging from 100 minutes prior to administration of the hepatotoxic agent to 50 minutes subsequent to administration of the hepatotoxic agent.

According to an aspect of some embodiments of the invention, there is provided a use of an alginate composition in the manufacture of a medicament for treating a liver damage induced by a hepatotoxic agent, the treating being effected prior to, concomitant with, or up to 50 minutes after administration of the hepatotoxic agent.

According to an aspect of some embodiments of the invention, there is to provided an alginate composition, for use in reducing or preventing a liver damage caused by a hepatotoxic agent, the alginate composition being for administration prior to, concomitant with, shortly after exposure to the hepatotoxic agent.

According to an aspect of some embodiments of the invention, there is provided an alginate composition, for use in treating a medical condition treatable by a hepatotoxic agent, the treating comprising co-administering a therapeutically effective amount of the hepatotoxic agent and a therapeutically effective amount of the alginate composition, the co-administering being effected such that the alginate composition is administered to a subject during a time period ranging from 100 minutes prior to administration of the hepatotoxic agent to 50 minutes subsequent to administration of the hepatotoxic agent.

According to an aspect of some embodiments of the invention, there is provided an alginate composition, for use in treating a medical condition selected from the group consisting of the medical conditions listed in Table 1 (right column) herein, the treating comprising co-administering a therapeutically effective amount of a hepatotoxic agent selected from the group consisting of the hepatotoxic drugs listed in Table 1 (left column), the aforementioned hepatotoxic drug being respective to the aforementioned condition, and a therapeutically effective amount of the alginate composition, the co-administering being effected such that the alginate composition is administered to a subject during a time period ranging from 100 minutes prior to administration of the hepatotoxic agent to 50 minutes subsequent to administration of the hepatotoxic agent.

According to an aspect of some embodiments of the invention, there is provided an alginate composition, for use in treating a liver damage induced by a hepatotoxic agent, the treating being effected prior to, concomitant with, or up to 50 minutes after administration of the hepatotoxic agent.

According to an aspect of some embodiments of the invention, there is provided a pharmaceutical composition comprising a therapeutically effective amount of a hepatotoxic agent and a therapeutically effective amount of an alginate composition, the alginate composition comprising a pharmaceutically acceptable carrier.

According to some embodiments of the invention, administration is effected up to 50 minutes after exposure to the hepatotoxic agent.

According to some embodiments of the invention, administration is effected during a time period ranging from 100 minutes prior to exposure to the hepatotoxic agent to 50 minutes subsequent to exposure to the hepatotoxic agent.

According to some embodiments of the invention, the treating is effected prior to, concomitant with, or up to 50 minutes after administration of the hepatotoxic agent.

According to some embodiments of the invention, the treating is effected during a time period ranging from 100 minutes prior to administration of the hepatotoxic agent to 50 minutes subsequent to administration of the hepatotoxic agent.

According to some embodiments of the invention, the alginate composition comprises a pharmaceutically acceptable carrier.

According to some embodiments of the invention, the carrier is an aqueous carrier.

According to some embodiments of the invention, the alginate composition is characterized by a solution viscosity in a range of from 3 to 50 mPa*seconds, at a shear rate of 1 second$^{-1}$ and at a concentration of 2% (w/v) alginate in the aqueous carrier.

According to some embodiments of the invention, the solution viscosity is in a range of from 3 to 20 mPa*seconds.

According to some embodiments of the invention, the alginate composition comprises alginate at a concentration in a range of from 0.4% to 10% (w/v).

According to some embodiments of the invention, the alginate composition comprises alginate characterized by a molecular weight in a range of from 10 to 75 kDa.

According to some embodiments of the invention, the molecular weight is in a range of from 30 to 50 kDa.

According to some embodiments of the invention, the alginate composition comprises alginate in a form of a sodium salt.

According to some embodiments of the invention, administration of the alginate composition is effected by systemic administration.

According to some embodiments of the invention, administration of the alginate composition is effected by oral administration.

According to some embodiments of the invention, administration of the alginate composition is effected by intraperitoneal administration.

According to some embodiments of the invention, administration of the alginate composition comprises co-administration of the alginate composition and the hepatotoxic agent.

According to some embodiments of the invention, the alginate composition and the hepatotoxic agent are co-formulated within the same composition.

According to some embodiments of the invention, the hepatotoxic agent is selected from the group consisting of ethanol, paracetamol, acarbose, amiodarone, bosentan, bromfenac, dantrolene, diclofenac, dihydralazine, disulfiram, felbamate, fluoxetine, halothane, isoniazid, kava, ketoconazole, labetalol, leflunomide, methotrexate, methyldopa, nefazodone, nicotinic acid, paroxetine, pemoline, propylthiouracil, pyrazinamide, rifampin, ritonavir, sertraline, statins, tacrine, tetracycline antibiotics, tolcapone, troglitazone, trovafloxacin, valproic acid, ximelagatran, zafirlukast, zileuton, anabolic steroids, azathioprine, azithromycin, captopril, cimetidine, ciprofloxacin, clopidogrel, dicloxacillin, erythromycin, estrogens, flucloxacillin, naproxen, phenobarbital, phenothiazine antipsychotics, phenytoin, sulindac, terbinafine, tricyclic antidepressants, amoxicillin-clavulanic acid, carbamazepine, cyclosporine, enalapril, flutamide, methimazole, nitrofurantoin, sulfonamides, trazodone, trimethoprim, verapamil, allopurinol, aspirin, betahistine, busulfan, cephalosporins, chlorpheniramine, clarithromycin, codeine, corticosteroids, cyclophosphamide, cytarabine, danazol, dihydrocodeine, fluconazole, hydralazine, indinavir, mahuang, mebeverine, metoclopramide, oxycodone, penicillamine, phenylbutazone, procainamide, quinidine, retinol, reverse transcriptase inhibitors, sulpiride, tamoxifen and telithromycin.

According to some embodiments of the invention, the hepatotoxic agent is paracetamol.

According to some embodiments of the invention, the hepatotoxic agent is ethanol.

According to some embodiments of the invention, the pharmaceutical composition is for treating a medical condition treatable by the hepatotoxic agent.

According to some embodiments of the invention, the alginate composition in the pharmaceutical composition is for reducing or preventing a liver damage caused by the hepatotoxic agent.

According to some embodiments of the invention, the composition is a unit dosage form.

According to some embodiments of the invention, the composition is formulated for systemic administration.

According to some embodiments of the invention, the composition is formulated for oral administration.

According to some embodiments of the invention, the composition is formulated for intraperitoneal administration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a bar graph showing serum ALT activity in mice 24 hours after administration of 4 mg paracetamol (APAP), with or without per os (PO) administration of 200 µl of a 2% solution of VLVG alginate, 30 minutes prior to administration of paracetamol ($p<0.0005$ between the two groups);

Figure 2A:
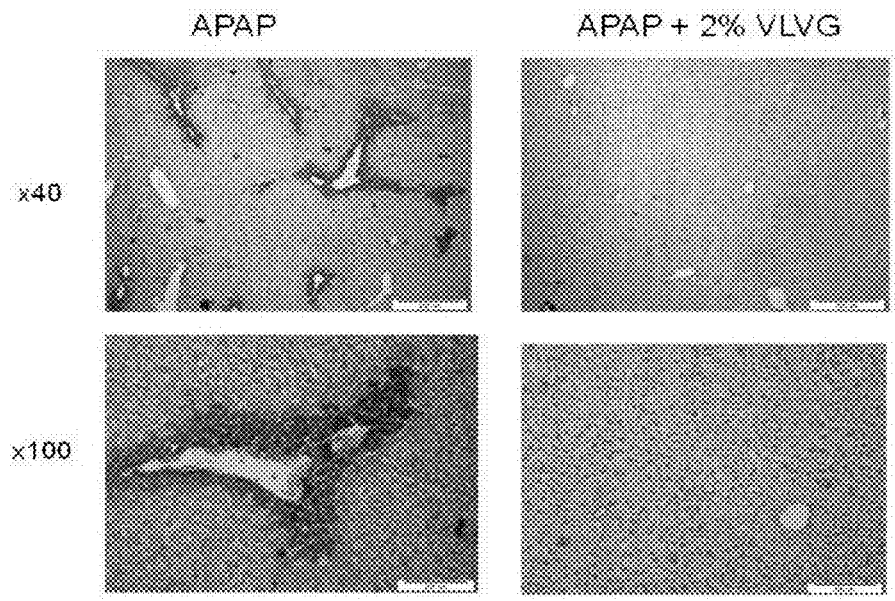
Figure 2B:
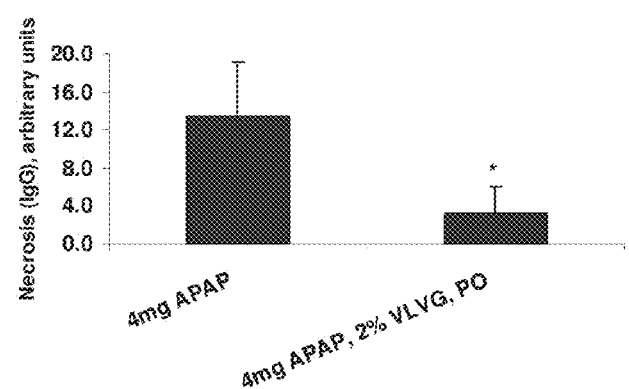
Figure 3:
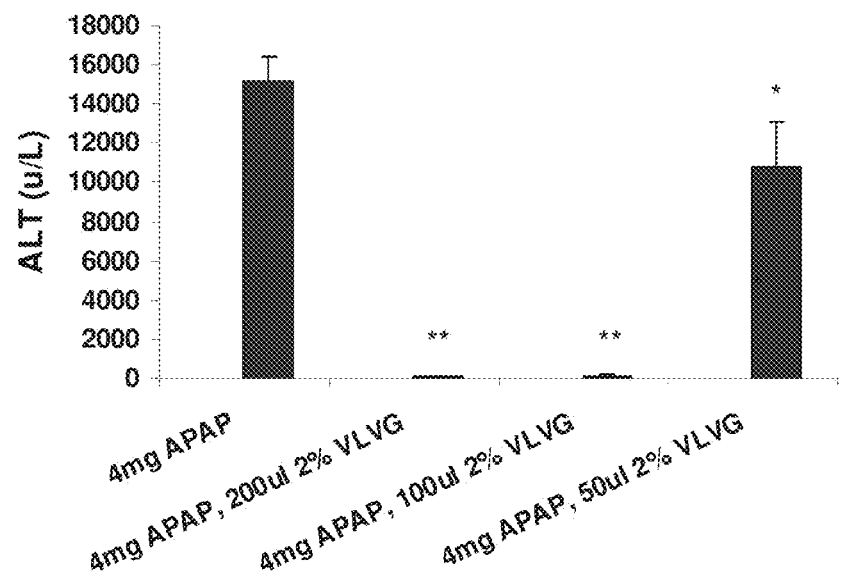
Figure 4:
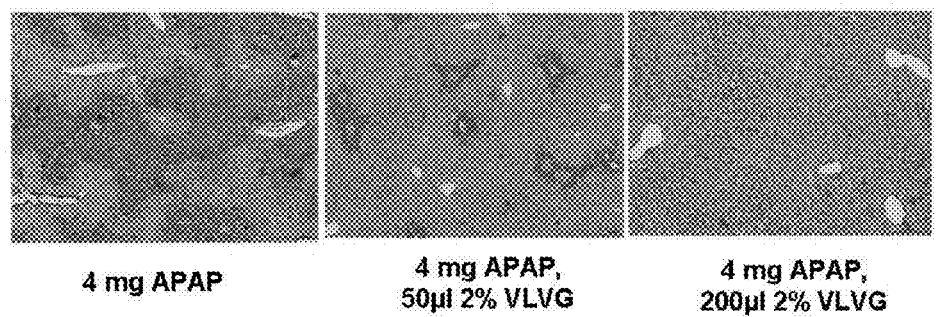
Figure 5:
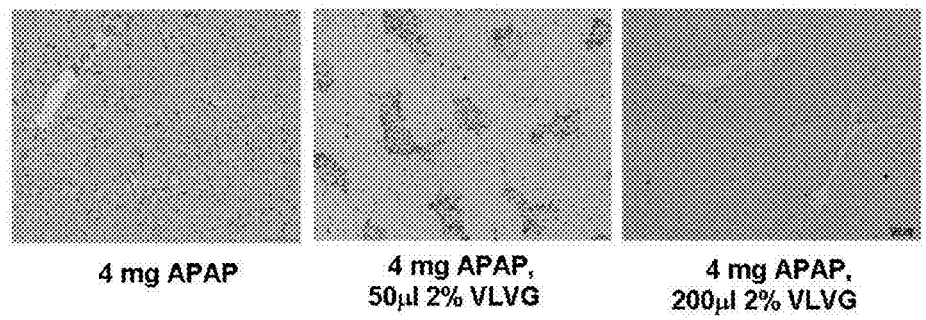
Figure 6:
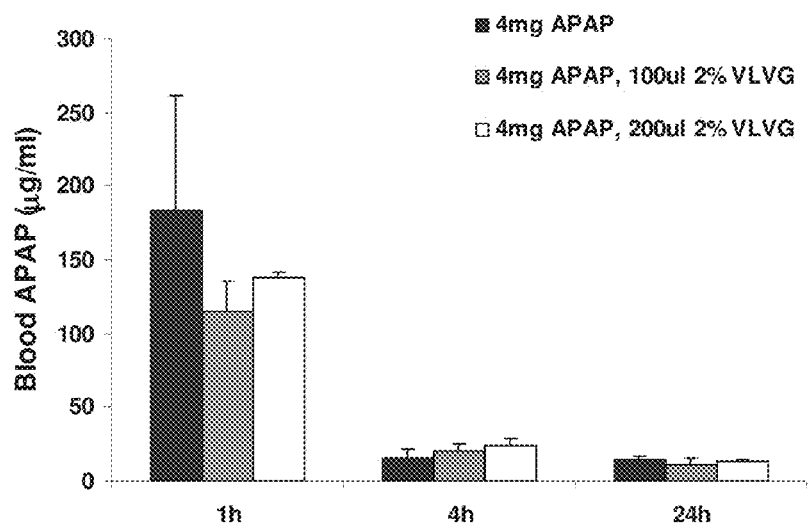
Figure 7:
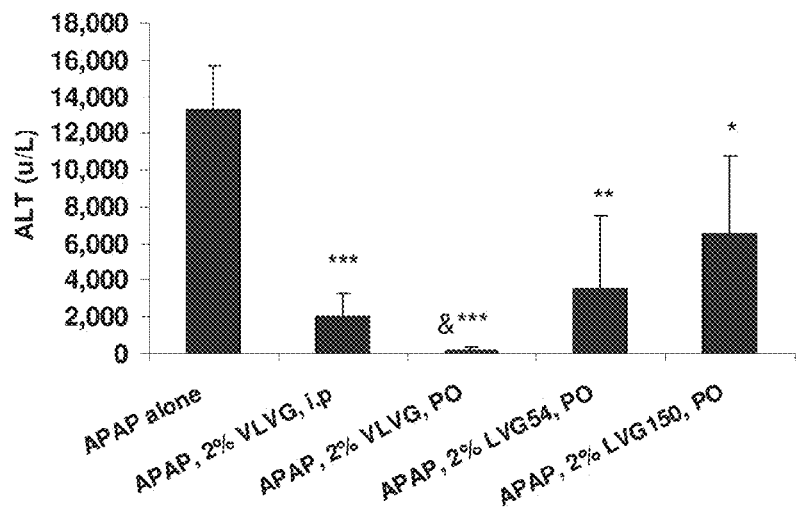
Figure 8:
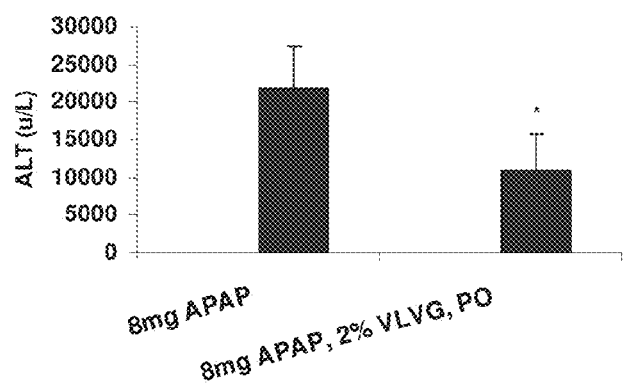
Figure 9:
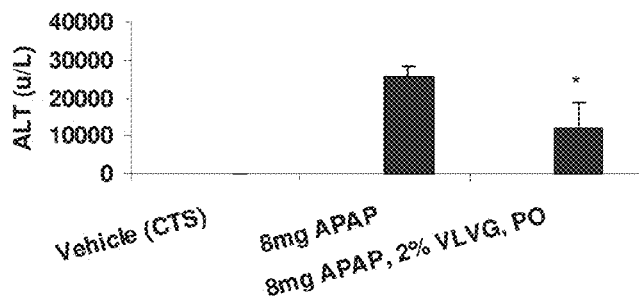
Figure 10:
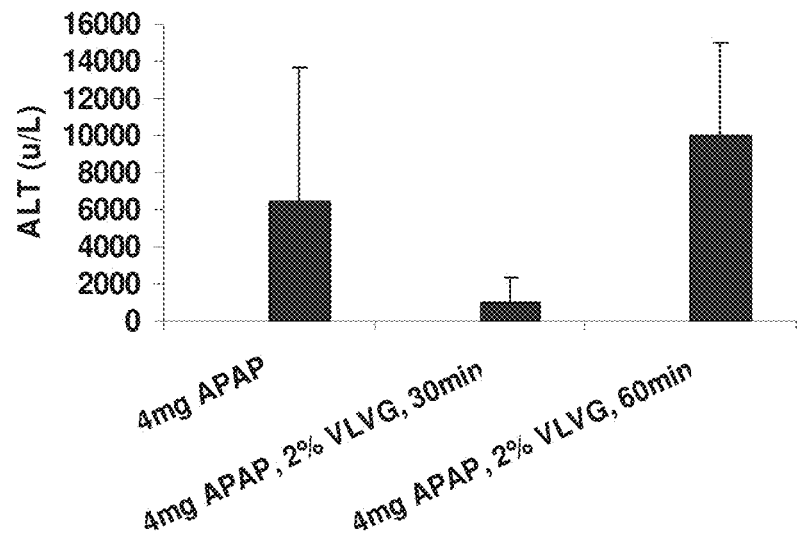
Figure 11:
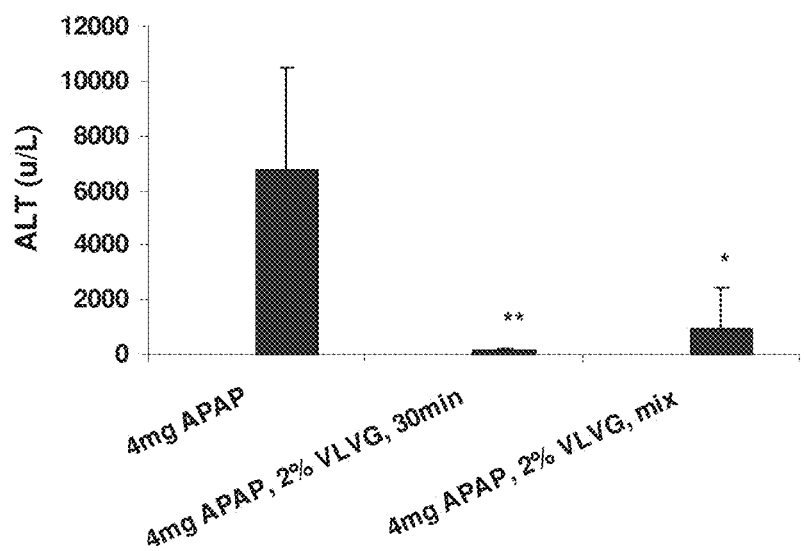
Figure 12:
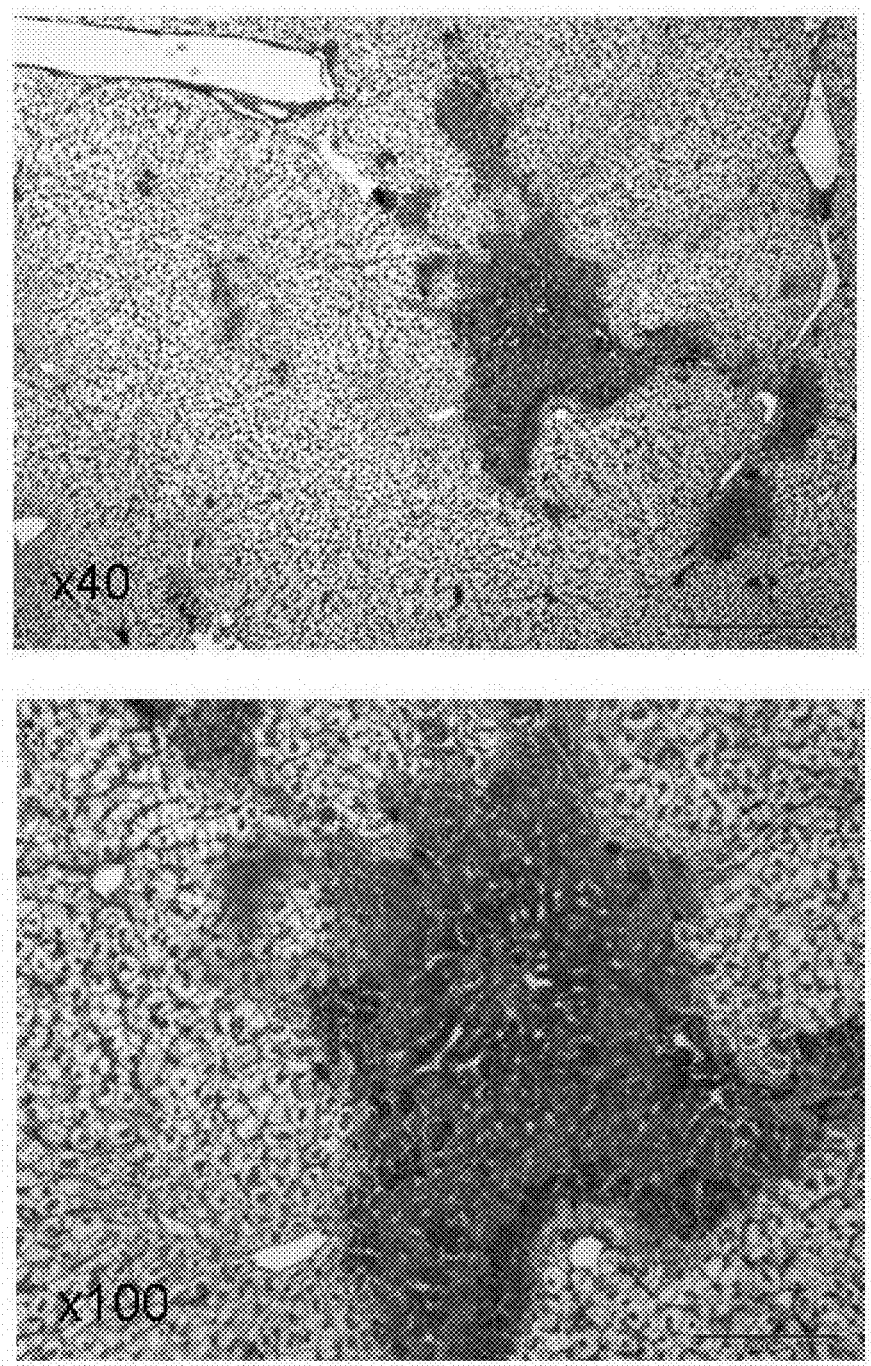
Figure 13A:
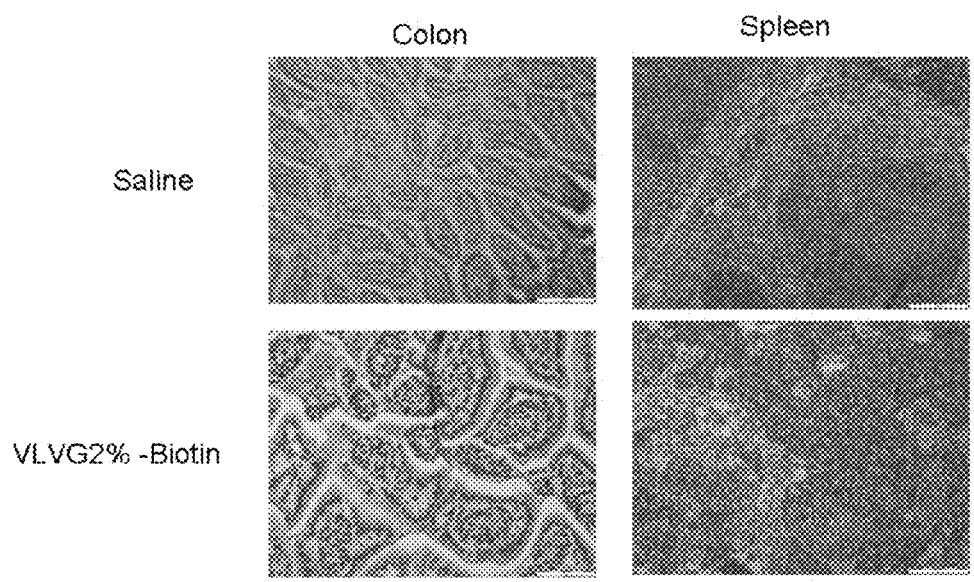
Figure 13B:
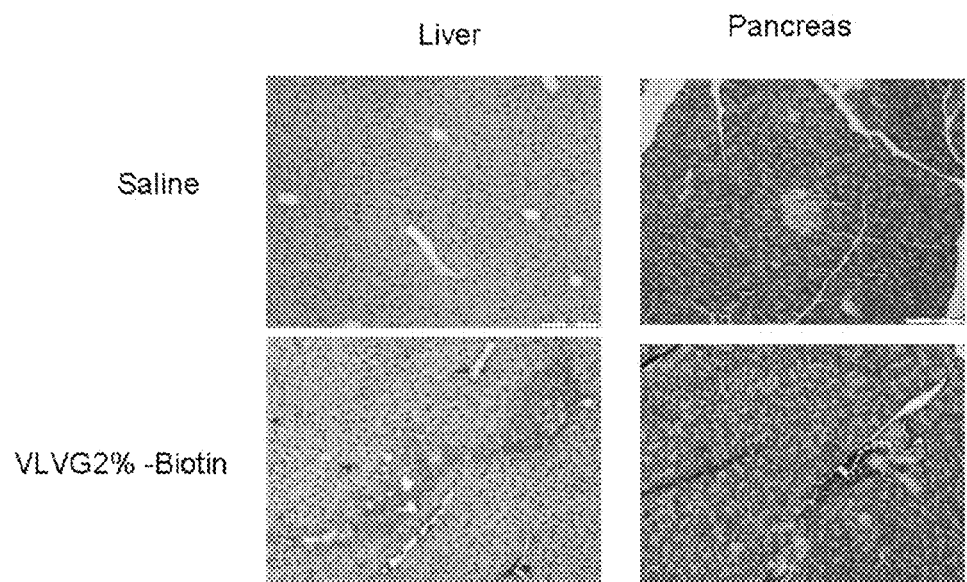

FIGS. 2A and 2B present images (FIG. 2A; magnified ×40 and ×100) showing staining with IgG of necrotic cells in liver tissue from mice after administration of 4 mg paracetamol (APAP), with or without per os (PO) administration of a 2% solution of VLVG alginate, 30 minutes prior to administration of paracetamol, as well as a bar graph (FIG. 2B) showing the amount of necrosis (scale bars are 500 µm for ×40 magnification and 200 µm for ×100 magnification, *$p<0.007$);

FIG. 3 is a bar graph showing serum ALT activity in mice 24 hours after administration of 4 mg paracetamol (APAP), with or without per os (PO) administration of a 50, 100 or 200 µl of a 2% solution of VLVG alginate, 30 minutes prior to administration of paracetamol (*$p<0.02$, **$p<0.000001$ relative to APAP alone);

FIG. 4 presents images (magnified ×100) showing staining of nitrotyrosine in liver tissue from mice after administration of 4 mg paracetamol (APAP), with or without per os (PO) administration of 50 µl or 200 µl of a 2% solution of VLVG alginate, 30 minutes prior to administration of paracetamol;

FIG. 5 presents images (magnified ×100) showing staining of Ki-67 in liver tissue from mice after administration of 4 mg paracetamol (APAP), with or without per os (PO) administration of 50 µl or 200 µl of a 2% solution of VLVG alginate, 30 minutes prior to administration of paracetamol;

FIG. 6 is a bar graph showing serum paracetamol (APAP) levels in mice 1, 4 and 24 hours after administration of 4 mg paracetamol, with per os (PO) administration of 100 µl or 200 µl of a 2% solution of VLVG alginate, 30 minutes prior to administration of paracetamol;

FIG. 7 is a bar graph showing serum ALT activity in mice 24 hours after administration of 4 mg paracetamol (APAP), with or without per os (PO) administration of 2% solutions of VLVG alginate, LVG54 alginate or LVG150 alginate, or i.p. administration of a 2% solution of VLVG alginate, 30 minutes prior to administration of paracetamol (*$p<0.05$, $p<0.01$, *$p<0.0002$ relative to APAP alone; & $p<0.04$ relative to 2% VLVG i.p. treatment);

FIG. 8 is a bar graph showing serum ALT activity in mice 24 hours after administration of 8 mg paracetamol (APAP), with or without per os (PO) administration of a 2% solution of VLVG alginate, 30 minutes prior to administration of paracetamol (*$p=0.005$ between the two groups);

FIG. 9 is a bar graph showing serum ALT activity in mice 24 hours after administration of vehicle or 8 mg paracetamol (APAP), with or without per os (PO) administration of a 2% solution of VLVG alginate, 30 minutes prior to administration of paracetamol or vehicle (*$p>0.004$ relative to APAP alone);

FIG. 10 is a bar graph showing serum ALT activity in mice 24 hours after administration of 4 mg paracetamol (APAP), with or without per os (PO) administration of a 2% solution of VLVG alginate, 30 or 60 minutes after administration of paracetamol ($p<0.002$ for difference between 30 and 60 minutes);

FIG. 11 is a bar graph showing serum ALT activity in mice 24 hours after administration of 4 mg paracetamol (APAP), with or without per os (PO) administration of a 2% solution of VLVG alginate, 30 minutes after administration of paracetamol or concurrently (mix) with paracetamol (*$p<0.01$, **$p<0.002$ relative to APAP without VLVG);

FIG. 12 presents images of immunohistochemical staining of biotin-labeled VLVG alginate in liver parenchyma (at magnifications of ×40 and ×100, scale bar represents 500 µm for magnification of ×40 and 200 µm for magnification of ×100); and FIGS. 13A and 13B present images showing presence of stained biotin in liver and pancreas (FIG. 13B) and absence of stained biotin in colon and spleen (FIG. 13A), following administration of a 2% solution of biotin-labeled VLVG alginate (no staining is visible after administration of saline as control, scale bars represent 200 µm).

DESCRIPTION OF SPECIFIC EMBODIMENTS OF THE INVENTION

The present invention, in some embodiments thereof, relates to therapy and, more particularly, but not exclusively, to novel therapeutic methodologies for reducing or preventing liver damage caused by hepatotoxic agents by utilizing alginate-based compositions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have investigated the effects of alginate on liver damage. Through serendipity, the inventors uncovered that systemically administered alginate is particularly effective at treating liver damage associated with chemical hepatotoxicity, when the alginate is administered prior to, concomitant with, or shortly after (e.g., less than 60 minutes after) exposure to hepatotoxicity. The inventors have further envisioned that although such a time frame is normally not particularly useful for treating liver diseases or disorders, the high degree of biocompatibility of alginate (which is widely used as a food additive) and the above-mentioned time frame during which alginate is particularly effective makes alginate unusually suitable for being administered prior to, shortly after, or in combination with exposure to hepatotoxic agents. In such a usage, liver damage may be reduced, nullified or even not induced, rendering administration of hepatotoxic agents without an alginate generally inadvisable.

Referring now to the drawings, FIGS. 1-5 and 7-9 show that oral administration of a solution of alginate reduces liver damage caused by paracetamol, when the alginate is administered prior to the paracetamol. FIGS. 3-5 show that a dose of 100 or 200 µl of a 2% solution of alginate in mice results in almost complete elimination of signs of hepatotoxicity caused by 4 mg paracetamol, whereas 50 µl is only partially effective. FIG. 6 shows that the reduction in liver damage is not due to any alteration of paracetamol absorption. FIG. 7 shows that very low viscosity alginate is the most potent alginate (compared to alginate characterized by higher viscosity), that oral administration and intraperitoneal administration of alginate are both effective, and that oral administration is particularly effective. FIGS. 8 and 9 show that the alginate protects against sub-lethal doses of paracetamol. FIG. 10 shows that the alginate exhibits a superior protection against liver damage when administered 30 minutes after paracetamol, (compared to alginate administered 60 minutes after paracetamol). FIG. 11 shows that the alginate protects against liver damage when administered concomitantly with, or 30 minutes after paracetamol. FIGS. 12-13B show that systemically administered alginate localizes in the liver, further indicating that alginate can act on the liver following systemic administration.

Hence, according to one aspect of embodiments of the invention, there is provided a method of protecting a subject from liver damage caused by a hepatotoxic agent, the method comprising administering to a subject exposed to the hepatotoxic agent a therapeutically effective amount of an alginate composition.

Herein, the phrase "protecting a subject from liver damage" refers to treating damage that has already been caused by reducing or eliminating the damage, and/or to preventing or reducing future liver damage.

It is to be understood that the protection may be due to a local effect (e.g., a direct effect of alginate in contact with liver tissue) and/or due to a systemic effect, such as a systemic anti-inflammatory effect (e.g., by reducing levels of pro-inflammatory cytokines).

As used herein, the terms "treat", "treating" and "treatment" encompass abrogating, substantially inhibiting, slowing or reversing the progression of a condition, substantially ameliorating clinical or aesthetical symptoms of a condition or substantially preventing or reduce the appearance of clinical or aesthetical symptoms of a condition.

Herein, the "subject" encompasses any subject who is exposed or is about to be exposed to a hepatotoxic agent, as further detailed hereinbelow. The subject may be already diagnosed as being previously exposed to the hepatotoxic agent and/or diagnosed with liver injury; subjects having a medical condition which is to be treated with a hepatotoxic agent and/or has already begun treatment with a hepatotoxic agent; and any subject at risk for liver injury associated with a hepatotoxic agent (e.g., an alcoholic).

By "exposed" it is meant that the subject has consumed a hepatotoxic agent (e.g., by administration of the hepatotoxic agent, or by eating, drinking or inhaling the hepatotoxic agent). If a hepatotoxic agent is administered, then "exposure" includes any time between administration and the presence of the agent or of metabolites thereof in the liver.

The subject may be any human or non-human animal. In some embodiments, the subject is a mammal. In exemplary embodiments, the subject is a human.

As used herein, the phrase "alginate composition" encompasses an alginate per se (e.g., as a solid), or an alginate within a carrier (e.g., a liquid carrier). The carrier may be a pure substance (e.g., a solvent) or may comprise additional ingredients (e.g., a solution consisting of a solvent and solutes).

In exemplary embodiments, an alginate composition as described herein contains an aqueous carrier, such that the composition comprises an aqueous solution of the alginate. The aqueous carrier may be, for example, water or an aqueous solution, such as a sodium chloride solution.

In some embodiments, the carrier is a pharmaceutically acceptable carrier.

As used herein, the phrase "therapeutically effective amount" generally describes an amount of the compound being administered which will relieve to some extent one or more of the symptoms of the condition being treated. The relief may be of an existing symptom and/or of a future symptom (e.g., a symptom of a condition which is to be prevented or reduced).

In the context of protecting a subject from liver damage, a therapeutically effective amount is sufficient to result in a reduction in liver damage by at least 25%, and preferably at least 50%, as compared to liver damage in individuals who are in a similar condition but are not administered alginate. Liver damage may be quantified according to serum levels of any biomolecule which is used in the art as a marker for liver damage (e.g., as exemplified herein), where liver damage is represented by the difference between measured serum levels of the biomolecule and the normal range for serum levels of the biomolecule (as recognized in the art). For example, when liver damage is indicated by serum levels of alanine transaminase (ALT) above the upper limit of normal (ULN), a reduction by 50% of the difference between serum levels of ALT and the ULN (in comparison with individuals not administered alginate) indicates a reduction of 50% in liver damage. In addition, to ALT, aspartate transaminase (AST), albumin, and alkaline phosphatase (ALP) are examples of markers used in the art for determining liver damage.

In the context of using a hepatotoxic agent (e.g., a hepatotoxic drug) to treat a medical condition treatable by the hepatotoxic agent, as described herein, a therapeutically effective amount is an amount which will relieve to some extent one or more of the symptoms of the condition treatable by the hepatotoxic agent, and which is an amount sufficient to cause liver damage in at least some subjects.

According to some embodiments, administration of the alginate composition is effected prior to, concomitant with, or shortly after exposure to the hepatotoxic agent.

In any aspect of embodiments of the invention described herein, a treatment regimen according to any of the embodiments described herein (e.g., with respect to a time and/or route of administration, and/or a condition being treated) may be used in association with an alginate according to any one of the embodiments described herein regarding an alginate, and/or with a hepatotoxic agent according to any of the embodiments described herein regarding a hepatotoxic agent, unless otherwise indicated.

Herein, "shortly after exposure" means up to 24 hours after exposure (i.e., not later than 24 hours after exposure). In some of any one of the embodiments described herein, administration is effected up to 12 hours after exposure. In some embodiments, administration is effected up to 6 hours after exposure. In some embodiments, administration is effected up to 4 hours after exposure. In some embodiments, administration is effected up to 3 hours after exposure. In some embodiments, administration is effected up to 2 hours after exposure.

In preferred embodiments from among any one of the embodiments described herein, administration is effected less than 1 hour after exposure. In some embodiments, administration is effected up to 50 minutes after exposure. In some embodiments, administration is effected up to 40 minutes after exposure. In some embodiments, administration is effected up to 30 minutes after exposure. In some embodiments, administration is effected up to 20 minutes after exposure. In some embodiments, administration is effected up to 10 minutes after exposure.

As used herein, the terms "concomitant" and "concomitantly" refer to an event (e.g., administration of an alginate composition) being performed as closely in time as is practically possible to another event (e.g., exposure to a hepatotoxic agent). In some embodiments, "concomitant" and "concomitantly" refer to events separated by no more than 1 hour. In some embodiments, "concomitant" and "concomitantly" refer to events separated by no more than 45 minutes. In some embodiments, "concomitant" and "concomitantly" refer to events separated by no more than 30 minutes. In some embodiments, "concomitant" and "concomitantly" refer to events separated by no more than 20 minutes. In some embodiments, "concomitant" and "concomitantly" refer to events separated by no more than 10 minutes.

In some of any one of the embodiments described herein, the alginate composition is administered no more than 24 hours prior to exposure to the hepatotoxic agent. In some embodiments, the alginate composition is administered no more than 12 hours prior to exposure to the hepatotoxic agent. In some embodiments, the alginate composition is administered no more than 6 hours prior to exposure to the hepatotoxic agent. In some embodiments, the alginate composition is administered no more than 3 hours prior to exposure to the hepatotoxic agent.

Exposure to the hepatotoxic agent may be effected, for example, by co-administration of the hepatotoxic agent (e.g., a hepatotoxic drug) and the alginate composition, as described herein.

In some of any one of the embodiments described herein, co-administration is such that the alginate composition is administered during a time period ranging from 100 minutes prior to exposure to the hepatotoxic agent to 50 minutes subsequent to exposure to the hepatotoxic agent. In some embodiments, the alginate composition is administered no more than 75 minutes prior to exposure to the hepatotoxic agent. In some embodiments, the alginate composition is administered no more than 50 minutes prior to exposure to the hepatotoxic agent. In some embodiments, the alginate composition is administered no more than 40 minutes prior to exposure to the hepatotoxic agent. In some embodiments, the alginate composition is administered no more than 30 minutes prior to exposure to the hepatotoxic agent. In some embodiments, the alginate composition is administered no more than 20 minutes prior to exposure to the hepatotoxic agent. In some embodiments, the alginate composition is administered no more than 10 minutes prior to exposure to the hepatotoxic agent.

In some of any one of the embodiments described herein, the alginate composition is administered no more than 40 minutes subsequent to exposure to the hepatotoxic agent. In some embodiments, the alginate composition is administered no more than 30 minutes subsequent to exposure to the hepatotoxic agent. In some embodiments, the alginate composition is administered no more than 20 minutes subsequent to exposure to the hepatotoxic agent. In some embodiments, the alginate composition is administered no more than 10 minutes subsequent to exposure to the hepatotoxic agent.

In some of any one of the embodiments described herein, the alginate composition is administered during a time period ranging from 75 minutes prior to exposure to the hepatotoxic agent to 50 minutes subsequent to exposure to the hepatotoxic agent. In some embodiments, the alginate composition is administered during a time period ranging from 50 minutes prior to exposure to the hepatotoxic agent to 40 minutes subsequent to exposure to the hepatotoxic agent. In some embodiments, the alginate composition is administered during a time period ranging from 40 minutes prior to exposure to the hepatotoxic agent to 40 minutes subsequent to exposure to the hepatotoxic agent. In some embodiments, the alginate composition is administered during a time period ranging from 30 minutes prior to exposure to the hepatotoxic agent to 30 minutes subsequent to exposure to the hepatotoxic agent. In some embodiments, the alginate composition is administered during a time period ranging from 20 minutes prior to exposure to the hepatotoxic agent to 20 minutes subsequent to exposure to the hepatotoxic agent. In some embodiments, the alginate composition is administered during a time period ranging from 10 minutes prior to exposure to the hepatotoxic agent to 10 minutes subsequent to exposure to the hepatotoxic agent.

In some of any one of the embodiments described herein wherein the alginate composition is administered subsequent to exposure to the hepatotoxic agent, the alginate composition is administered during a time period ranging from 10 to 50 minutes subsequent to exposure to the hepatotoxic agent. In some embodiments, the alginate composition is administered during a time period ranging from 20 to 40 minutes subsequent to exposure to the hepatotoxic agent. In exemplary embodiments, the alginate composition is administered about 30 minutes subsequent to exposure to the hepatotoxic agent. In some embodiments, the alginate composition is administered during a time period ranging from 100 minutes prior to exposure to the hepatotoxic agent to 50 minutes subsequent to exposure to the hepatotoxic agent. In some embodiments, the alginate composition is administered during a time period ranging from 100 minutes prior to exposure to the hepatotoxic agent to 50 minutes subsequent to exposure to the hepatotoxic agent.

Without being bound by any particular theory, it is believed that the alginate composition is particularly effective when the time during which alginate is present in the liver of the subject overlaps considerably with the time during which the liver is exposed to dangerous levels of the hepatotoxic agent, or a hepatotoxic metabolite of the agent. For example, paracetamol hepatotoxicity is mediated by accumulation of hepatotoxic metabolites (e.g., N-acetyl-p-benzoquinone imine) in the liver following glutathione depletion, and such accumulation begins somewhat later (e.g., 15 minutes later) than the actual ingestion of the paracetamol.

In some of any of the embodiments described herein, protecting the subject from the liver damage comprises reducing or preventing a liver damage caused by the hepatotoxic agent.

In some of any one of the embodiments described herein, the method reduces by at least 25%, and preferably by at least 50%, the amount liver damage caused by the hepatotoxic agent subsequently to the time at which the alginate composition is administered. Liver damage caused by the hepatotoxic agent subsequently to administration of the alginate composition is determined according to changes in levels of a marker (e.g., as described herein) for liver damage after the time of alginate administration.

In some of any one of the embodiments described herein, the method is for treating a medical condition treatable by the hepatotoxic agent (e.g., a hepatotoxic drug) in a subject in need thereof. In such embodiments, the method comprises co-administering to the subject a therapeutically effective amount of the hepatotoxic agent (so as to treat the medical condition) and the alginate composition (so as to reduce or prevent liver damage by the therapeutically effective amount of the hepatotoxic agent). The therapeutically effective amount of the hepatotoxic agent is sufficient to be capable of causing liver damage, as described herein.

In some of any one of the embodiments described herein, the method is for treating a liver damage induced by a hepatotoxic agent. In some embodiments, the liver damage induced by a hepatotoxic agent is a drug-induced liver injury (DILI), as this term is defined in the art, the hepatotoxic agent being a drug.

In some of any one of the embodiments described herein, the liver damage (e.g., DILI) is characterized by relatively predictable reactions, for example, hepatotoxicity is dose-related, has a high incidence, occurs with a short latency (within a few days), results from direct toxicity of the hepatotoxic agent (e.g., a hepatotoxic drug) or its metabolite and/or is reproducible in animal models. Paracetamol is an exemplary agent which induces DILI characterized by a predictable reaction.

In some of any one of the embodiments described herein, the liver damage (e.g., DILI) is characterized by idiosyncratic reactions, for example, occurs with variable latency (at least 1 week), has a low incidence, hepatotoxicity may not be dose-related, levels of ALT are more than 3 times the upper limit of normal (ULN) and/or alkaline phosphatase (ALP) levels are more than twice the ULN. Most hepatotoxic drugs are associated with DILI characterized by idiosyncratic reactions.

In some of any one of the embodiments described herein, the liver damage (e.g., DILI) is mediated by an immune reaction.

In some of any one of the embodiments described herein, the liver damage (e.g., DILI) is not mediated by an immune reaction.

The hepatotoxic agent described herein throughout may be any therapeutically active agent known in the art of medicine which can cause liver damage (examples of which are described in detail below), as well as any other substance which is hepatotoxic when consumed. Examples of such substances include, without limitation, alcohol (e.g., ethanol) and beverages which contain alcohol (e.g., beer, wine, liquors), as well as chemicals found in industry and in household products (e.g., methanol, carbon tetrachloride, vinyl chloride and other volatiles, and arsenic).

Exposure to alcohol by self-administration (e.g., drinking alcoholic beverages) is very common, and is a leading cause of liver damage. In some embodiments, the alginate composition is included in an alcoholic beverage (e.g., beer, wine, liquor) or in any other alcoholic composition which may be drunk (e.g., rubbing alcohol), so as to prevent or reduce liver damage caused by the alcohol.

In some of any one of the embodiments described herein, the hepatotoxic agent is a therapeutically active agent (e.g., a conventional drug), namely, an agent administered in order to treat a medical condition. Examples of hepatotoxic drugs and medical conditions treatable by the drugs are presented in Table 1.

TABLE 1

| Hepatotoxic drug | Medical condition(s) treatable by drug |
|---|---|
| Paracetamol (acetaminophen, APAP) | Fever; pain |
| Acarbose | Diabetes |
| Amiodarone | Cardiac arrhythmia |
| Bosentan | Hypertension |
| Bromfenac | Inflammation; pain |
| Dantrolene | Malignant hyperthermia; neuroleptic malignant syndrome; muscle spasticity; Ecstasy intoxication; serotonin syndrome; 2,4-dinitrophenol poisoning |

TABLE 1-continued

| Hepatotoxic drug | Medical condition(s) treatable by drug |
|---|---|
| Diclofenac | Pain; inflammation; dysmenorrhea |
| Dihydralazine | Hypertension |
| Disulfiram | Alcohol dependence; cocaine dependence; scabies; protozoal infections |
| Felbamate | Epilepsy |
| Fluoxetine | Depression; obsessive-compulsive disorder; eating disorders; panic disorder; body dysmorphic disorder; premenstrual dysphoric disorder; trichotillomania; cataplexy; alcohol dependence |
| Halothane | Surgery |
| Isoniazid | Bacterial infections |
| Kava | Anxiety disorder |
| Ketoconazole | Fungal infections; alopecia |
| Labetalol | Hypertension |
| Leflunomide | Rheumatoid arthritis; psoriatic arthritis |
| Methotrexate | Cancer; rheumatoid arthritis; psoriasis; psoriatic arthritis; lupus; inflammatory bowel disease; pregnancy; ectopic pregnancy |
| Methyldopa | Hypertension; pre-eclampsia |
| Nefazodone | Depression; migraine |
| Nicotinic acid | Pellagra; atherosclerosis |
| Paroxetine | Depression; obsessive-compulsive disorder; post-traumatic stress disorder; panic disorder; anxiety disorder; premenstrual dysphoric disorder; premature ejaculation |
| Pemoline | Narcolepsy; attention-deficit hyperactivity disorder |
| Propylthiouracil | Hyperthyroidism |
| Pyrazinamide | Bacterial infections |
| Rifampin | Bacterial infections; cholestatic pruritis; vaccinia virus infection |
| Ritonavir | Retroviral infections |
| Sertraline | Depression; obsessive-compulsive disorder; post-traumatic stress disorder; panic disorder; body dysmorphic disorder; anxiety disorder; eating disorders; premenstrual dysphoric disorder; syncope |
| Statins | Cardiovascular disease |
| Tacrine | Alzheimer's disease |
| Tetracycline antibiotics | Bacterial infections; malaria; balantidiasis |
| Tolcapone | Parkinson's disease |
| Troglitazone | Diabetes |
| Trovafloxacin | Bacterial infections |
| Valproic acid | Epilepsy; bipolar disorder; depression; migraine; schizophrenia; colorectal polyps; basal cell carcinoma; acne; Alzheimer's disease |
| Ximelagatran | Deep venous thrombosis; venous thromboembolism; atrial fibrillation |
| Zafirlukast | Asthma |
| Zileuton | Asthma |
| Anabolic steroids | Hypoplastic anemia; growth failure; cancer; AIDS; delayed puberty; bone loss; gender identity disorder |
| Azathioprine | Graft-versus-host reaction; rheumatoid arthritis; pemphigus; lupus; Behcet's disease; autoimmune hepatitis; atopic dermatitis; myasthenia gravis; neuromyelitis optica; restrictive lung disease; inflammatory bowel disease; multiple sclerosis |
| Azithromycin | Bacterial infections; toxoplasmosis; malaria |
| Captopril | Hypertension; congestive heart failure; diabetic nephropathy |
| Cimetidine | Heartburn; peptic ulcer; herpes zoster; calcific tendinitis; interstitial cystitis; cancer |
| Ciprofloxacin | Bacterial infections |
| Clopidogrel | Atherosclerosis; coronary artery disease; peripheral vascular disease; cerebrovascular disease; coronary stent implantation |

TABLE 1-continued

| Hepatotoxic drug | Medical condition(s) treatable by drug |
|---|---|
| Dicloxacillin | Bacterial infections |
| Erythromycin | Bacterial infections |
| Estrogens | Pregnancy |
| Flucloxacillin | Bacterial infections |
| Naproxen | Fever; pain; inflammation; dysmenorrhea |
| Phenobarbital | Epilepsy; benzodiazepine dependence; Gilbert's syndrome; cyclic vomiting syndrome |
| Phenothiazine antipsychotics | Schizophrenia; acute psychosis; bipolar disorder; hallucination; delusion disorder; congestive heart failure; porphyria; tetanus; amoebic meningoencephalitis; insomnia; pruritus; migraine; opioid addiction |
| Phenytoin | Epilepsy |
| Sulindac | Pain; inflammation; colorectal polyps; preterm labor; Alzheimer's disease |
| Terbinafine | Fungal infections |
| Tricyclic antidepressants | Depression; anxiety disorder; obsessive-compulsive disorder; panic disorder; post-traumatic stress disorder; body dysmorphic disorder; personality disorder; attention-deficit hyperactivity disorder; eating disorders; bipolar disorder; pain; neuralgia; fibromyalgia; migraine; smoking addiction; Tourette syndrome; trichotillomania; irritable bowel syndrome; interstitial cystitis; nocturnal enuresis; narcolepsy; insomnia; pathological crying and/or laughing; chronic hiccups; ciguatera poisoning; schizophrenia; biliary dyskinesia |
| Amoxicillin-clavulanic acid | Bacterial infections |
| Carbamazepine | Epilepsy; bipolar disorder; neuropathic pain; attention-deficit hyperactivity disorder; schizophrenia; phantom limb syndrome; complex regional pain syndrome; paroxysmal extreme pain disorder; neuromyotonia; intermittent explosive disorder; personality disorder; myotonia congenita; post-traumatic stress disorder |
| Cyclosporine | Graft-versus-host reaction; psoriasis; atopic dermatitis; pyoderma gangrenosum; autoimmune urticaria; rheumatoid arthritis; dry eye |
| Enalapril | Hypertension; chronic heart failure |
| Flutamide | Prostate cancer |
| Methimazole | Hyperthyroidism |
| Nitrofurantoin | Bacterial infections |
| Sulfonamides | Bacterial infections; retroviral infections; diabetes; heart failure; liver cirrhosis; hypertension; glaucoma; epilepsy; altitude sickness; cystinuria; dural ectasia; periodic paralysis; osteoarthritis; rheumatoid arthritis; pain; colorectal polyps; burns; gout; hyperuricemia; cardiac arrhythmia; inflammatory bowel disease; migraine |
| Trazodone | Depression; bipolar disorder; anxiety disorder; insomnia; fibromyalgia; panic disorder; diabetic neuropathy; eating disorders; obsessive-compulsive disorder; alcohol dependence; schizophrenia; complex regional pain syndrome |
| Trimethoprim | Bacterial infections |
| Verapamil | Hypertension; angina pectoris; cardiac arrhythmia; cluster headache; migraine; malaria |
| Allopurinol | Hyperuricemia; gout; tumor lysis syndrome; ischemic reperfusion injury; uric acid nephrolithiasis; protozoal infections; epilepsy; hypertension |
| Aspirin | Pain; migraine; fever; cardiovascular disease; percutaneous coronary intervention; cancer; rheumatic fever; Kawasaki disease |

TABLE 1-continued

| Hepatotoxic drug | Medical condition(s) treatable by drug |
|---|---|
| Betahistine | Meniere's disease; balance disorder |
| Busulfan | Cancer |
| Cephalosporins | Bacterial infections |
| Chlorpheniramine | Allergy |
| Clarithromycin | Bacterial infections |
| Codeine | Pain; cough; diarrhea; irritable bowel syndrome |
| Corticosteroids | Adrenal insufficiency; congenital adrenal hyperplasia; pain; inflammation; arthritis; temporal arteritis; dermatitis; allergy; asthma; hepatitis; lupus; inflammatory bowel disease; sarcoidosis; Addison's disease; brain tumor |
| Cyclophosphamide | Cancer; lupus; rheumatoid arthritis; Wegener's granulomatosis; multiple sclerosis |
| Cytarabine | Cancer; herpesvirus infection |
| Danazol | Endometriosis; menorrhagia; fibrocystic breast disease; immune thrombocytopenic purpura; mastodynia; hereditary angioedema |
| Dihydrocodeine | Pain; cough; dyspnea; irritable bowel syndrome; opioid addiction |
| Fluconazole | Fungal infections |
| Hydralazine | Hypertension |
| Indinavir | Retroviral infections |
| Ma-huang | Excess weight |
| Mebeverine | Irritable bowel syndrome |
| Metoclopramide | Nausea; vomiting; gastroparesis; migraine |
| Oxycodone | Pain; diarrhea; irritable bowel syndrome |
| Penicillamine | Rheumatoid arthritis; Wilson's disease; cystinuria; scleroderma; arsenic poisoning |
| Phenylbutazone | Fever; pain |
| Procainamide | Cardiac arrhythmia |
| Quinidine | Cardiac arrhythmia; malaria |
| Retinol | Acne; acute promyelocytic leukemia; vitamin A deficiency |
| Reverse transcriptase inhibitors | Retroviral infections |
| Sulpiride | Schizophrenia; depression |
| Tamoxifen | Cancer; McCune-Albright syndrome; anovulatory disorder; retroperitoneal fibrosis; gynecomastia; bipolar disorder; Riedel's thyroiditis |
| Telithromycin | Bacterial infections |

Thus, in some of any one of the embodiments described herein, the method is for treating any of the medical conditions listed in Table 1 (right column), and is effected by co-administering to the subject a therapeutically effective amount of a hepatotoxic agent that is respective to (e.g., suitable for treating) the medical condition (as listed in Table 1 (left column)) and a therapeutically effective amount of an alginate composition.

Examples of hepatotoxic anabolic steroids include, without limitation, 4-androstenedione, androstenone, boldenone, fluoxymesterone, methandienone, methandrostenolone, methyltestosterone, nandrolone decanoate, nortestosterone, oxandrolone, oxymetholone, testosterone and trenbolone.

Examples of hepatotoxic cephalosporins include, without limitation, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxome, cefoperazone, ceftazidime, cefclidine, cefepime, cefluprenam, cefoselis, cefozopran, cefpirome, cefquinome, ceftobiprole and ceftaroline.

Examples of hepatotoxic corticosteroids include, without limitation, aclometasone dipropionate, amcinonide, betamethasone, betamethasone dipropionate, betamethasone sodium phosphate, betamethasone valerate, budesonide, clobetasone-17-butyrate, clobetasol-17-propionate, cortisone acetate, desonide, dexamethasone, dexamethasone sodium phosphate, fludrocortisone, fluocinonide, fluocinonide acetonide, fluocortolone, fluocortolone caproate, fluocortolone pivalate, fluprednidene acetate, halcinonide, hydrocortisone, hydrocortisone-17-aceponate, hydrocortisone acetate, hydrocortisone-17-buteprate, hydrocortisone-17-butyrate, hydrocortisone-17-valerate, methylprednisolone, mometasone, prednicarbate, prednisolone, prednisone, tixocortol pivalate, triamcinolone acetonide, and triamcinolone alcohol.

Examples of hepatotoxic estrogens include, without limitation, oral contraceptive ingredients such as ethinyl estradiol, estradiol valerate and mestranol. The estrogen may be formulated alone or in a form of a combined oral contraceptive, as is common in the art.

Examples of hepatotoxic phenothiazine antipsychotics include, without limitation, promethazine, chlorpromazine, promazine, triflupromazine, methotrimeprazine, mesoridazine, thioridazine, fluphenazine, perphenazine, prochlorperazine and trifluoperazine. In some embodiments, the phenothiazine antipsychotic is chlorpromazine. Conditions treatable by chlorpromazine include, without limitation, schizophrenia; acute psychosis; bipolar disorder; porphyria; tetanus; amoebic meningoencephalitis; insomnia; pruritus; migraine; and opioid addiction.

Examples of hepatotoxic reverse transcriptase inhibitors include, without limitation, nevirapine and nucleoside analog reverse transcriptase inhibitors (NRTIs) such as abacavir, apricitabine, didanosine, emtricitabine, entecavir, lamivudine, nevirapine, stavudine, zalcitabine and zidovudine.

Examples of hepatotoxic statins include, without limitation, atorvastatin, cerivastatin, fluvastatin, lovastatin, mevastatin, pitavastatin, rosuvastatin and simvastatin.

Examples of hepatotoxic sulfonamides include, without limitation, anti-bacterial drugs such as sulfamethoxazole, sulfisomidine, sulfacetamide, sulfadoxine and dichlorphenamide; anti-diabetic agents such as carbutamide, acetohexamide, chlorpropamide, tolbutamide, tolazamide, glipizide, gliclazide, glibenclamide, glibomuride, gliquidone, glisoxepide, glyclopyramide and glimepiride; diuretics such as acetazolamide, ethoxzolamide, sultiame and zonisamide; protease inhibitors such as darunavir, amprenavir, fosamprenavir and tipranavir; mafenide; celecoxib; probenecid; sotalol; sulfasalazine; and sumatriptan.

Examples of hepatotoxic tetracycline antibiotics include, without limitation, tetracycline, chlortetracycline, oxytetracycline, demeclocycline, doxycycline, lymecycline, meclocycline, methacycline, minocycline, PTK 0796, rolitetracycline and tigecycline.

Examples of hepatotoxic tricyclic antidepressants include, without limitation, amitriptyline, amitriptylinoxide, butriptyline, clomipramine, demexiptiline, desipramine, dibenzepin, dimetacrine, dosulepin, imipramine, imipraminoxide, lofepramine, melitracen, metapramine, nitroxezapine, nortriptyline, noxiptiline, pipofezine, propizepine, protriptyline, quinupramine, amineptine, iprindole, opipramol, tianeptine and trimipramine. In some embodiments, the tricyclic antidepressant is amitriptyline. Conditions treatable by amitriptyline include, without limitation, depression; anxiety disorder; attention-deficit hyperactivity disorder; migraine; eating disorders; bipolar disorder; neuralgia; insomnia; nocturnal enuresis; pain; and biliary dyskinesia.

Eating disorders treatable by the hepatotoxic drugs described herein (see, Table 1) include, without limitation, bulimia nervosa, anorexia nervosa, night eating syndrome, obesity, and binge eating disorder.

Examples of anxiety disorder treatable by hepatotoxic drugs described herein (see, Table 1) include, without limitation, generalized anxiety disorder and social anxiety disorder.

Borderline personality disorder is a non-limiting example of a personality disorder treatable by hepatotoxic drugs described herein.

In some of any one of the embodiments described herein, the liver damage is characterized by hepatocellular injury and/or hepatitis. Examples of hepatotoxic agents which can cause such liver damage include, without limitation, ethanol, paracetamol, acarbose, amiodarone, bosentan, bromfenac, dantrolene, diclofenac, dihydralazine, disulfiram, felbamate, fluoxetine, halothane, isoniazid, kava, ketoconazole, labetalol, leflunomide, methotrexate, methyldopa, nefazodone, nicotinic acid, paroxetine, pemoline, propylthiouracil, pyrazinamide, rifampin, ritonavir, sertraline, statins, tacrine, tetracycline antibiotics, tolcapone, troglitazone, trovafloxacin, valproic acid, ximelagatran, zafirlukast, and zileuton. Paracetamol is an exemplary hepatotoxic agent.

In some of any one of the embodiments described herein, the liver damage is characterized by cholestasis. Examples of hepatotoxic agents which can cause such liver damage include, without limitation, anabolic steroids, azathioprine, azithromycin, captopril, chlorpromazine, cimetidine, ciprofloxacin, clopidogrel, dicloxacillin, erythromycin, estrogens, flucloxacillin, naproxen, phenobarbital, phenothiazine antipsychotics, phenytoin, sulindac, terbinafine, and tricyclic antidepressants.

In some of any one of the embodiments described herein, the liver damage is characterized by a combination of hepatitis and cholestasis. Examples of hepatotoxic agents which can cause such liver damage include, without limitation, amitriptyline, amoxicillin-clavulinic acid, carbamazepine, cyclosporine, enalapril, flutamide, methimazole, nitrofurantoin, sulfonamides, trazodone, trimethoprim, and verapamil.

In some of any one of the embodiments described herein, the liver damage is to characterized by fibrosis and/or cirrhosis. Methotrexate is an exemplary hepatotoxic agent which can cause such liver damage.

In some of any one of the embodiments described herein, the liver damage is characterized by granulomas. Examples of hepatotoxic agents which can cause such liver damage include, without limitation, allopurinol, amoxicillin-clavulanic acid, carbamazepine, hydralazine, methyldopa, penicillamine, phenylbutazone, phenytoin, procainamide, quinidine and sulfonamides.

In some of any one of the embodiments described herein, the liver damage is characterized by microvesicular steatosis. Examples of hepatotoxic agents which can cause such liver damage include, without limitation, nucleoside analog reverse transcriptase inhibitors (e.g., such as described herein) and valproate.

In some of any one of the embodiments described herein, the liver damage is characterized by neoplasms. Examples of hepatotoxic agents which can cause such liver damage include, without limitation, anabolic steroids and estrogens.

In some of any one of the embodiments described herein, the liver damage is characterized by non-alcoholic steatohepatitis. Examples of hepatotoxic agents which can cause such liver damage include, without limitation, amiodarone and tamoxifen.

In some of any one of the embodiments described herein, the liver damage is characterized by vascular lesions. Examples of hepatotoxic agents which can cause such liver damage include, without limitation, anabolic steroids, estrogens, azathioprine, retinol, methotrexate, busulfan and cyclophosphamide.

According to another aspect of embodiments of the invention, there is provided a use of an alginate composition in the manufacture of a medicament for protecting a subject from liver damage caused by a hepatotoxic agent (e.g., an agent described herein). Treatment utilizing the medicament is effected by administering the medicament prior to, concomitant with, or shortly after (e.g., up to 50 minutes after) exposure to the hepatotoxic agent (e.g., in accordance with a method described herein).

In some of any one of the embodiments described herein, the medicament is for reducing or preventing a liver damage caused by the hepatotoxic agent, as described herein.

In some of any one of the embodiments described herein, the medicament is for treating a medical condition treatable by a hepatotoxic agent, as described herein. Such treating comprises co-administering, as described herein, a therapeutically effective amount of the hepatotoxic agent and a therapeutically effective amount of alginate composition.

In some of any one of the embodiments described herein, the medicament is for treating a medical condition such as the medical conditions listed in Table 1 (right column). Such treating comprises co-administering a therapeutically effective amount of a hepatotoxic agent respective to (or suitable for treating) the medical condition (e.g., a hepatotoxic drug as listed in Table 1 (left column)), as described herein, and a therapeutically effective amount of an alginate composition.

In some of any one of the embodiments described herein, the medicament is for treating a liver damage induced by a hepatotoxic agent (e.g., a drug-induced liver injury), as described herein.

According to another aspect of embodiments of the invention, there is provided an alginate composition for use in protecting a subject from liver damage caused by a hepatotoxic agent (e.g., an agent described herein). Treatment utilizing the alginate composition effected by administering the alginate composition prior to, concomitant with, or shortly after (e.g., up to 50 minutes after) exposure to the hepatotoxic agent (e.g., in accordance with a method described herein).

In some of any one of the embodiments described herein, the alginate composition is for reducing or preventing a liver damage caused by the hepatotoxic agent, as described herein.

In some of any one of the embodiments described herein, the alginate composition is for treating a medical condition treatable by a hepatotoxic agent, as described herein. Such treating comprises co-administering, as described herein, a therapeutically effective amount of the hepatotoxic agent, as described herein and a therapeutically effective amount of the alginate composition.

In some of any one of the embodiments described herein, the alginate composition is for treating a medical condition such as the medical conditions listed in Table 1 (right column). Such treating comprises co-administering a therapeutically effective amount of a hepatotoxic agent respective to (or suitable for treating) the medical condition as listed in Table 1 (left column), as described herein, and a therapeutically effective amount of the alginate composition.

In some of any one of the embodiments described herein, the alginate composition is for treating a liver damage induced by a hepatotoxic agent (e.g., drug-induced liver injury), as described herein.

The administration of the alginate composition (e.g., in a form of a medicament described herein) may be during any time period for administration described herein. For example, in some of any one of the embodiments described herein, co-administration is effected by administering the alginate composition/medicament during a time period ranging from 100 minutes prior to exposure to the hepatotoxic agent to 50 minutes subsequent to exposure to the hepatotoxic agent (e.g., as described herein).

In some of any one of the embodiments described herein of any of the aspects of embodiments of the invention described herein, administration of the alginate composition comprises co-administration of a therapeutically effective amount of the alginate composition and a therapeutically effective amount of the hepatotoxic agent.

The co-administration of a therapeutically effective amount of a hepatotoxic agent with an alginate composition is superior to current methodologies and regimens for administration of therapeutically effective amounts of hepatotoxic agents, in view of the hepatoprotection provided by the alginate. The co-administration described herein may therefore be effected without required monitoring of liver function, or with less frequent monitoring, in a subject being co-administered the hepatotoxic agent and alginate composition, in contrast to current methodologies (e.g., in which a subject is administered the hepatotoxic agent without an alginate composition). Hence, in some embodiments, a treatment of a medical condition as described herein is devoid of monitoring liver function or is effected while monitoring liver function less frequent (compared to subjects receiving the hepatotoxic drug without an alginate composition as described herein). For example, for a subject receiving a hepatotoxic drug for treating a chronic medical condition, liver function is monitored once every 6 month, or even a year, of treatment.

In some of any one of the embodiments described herein, the alginate composition and a therapeutically effective amount of the hepatotoxic agent are formulated separately (e.g., as two separate pharmaceutical compositions). The alginate composition may optionally be formulated as described herein (e.g., a medicament described herein), and the hepatotoxic agent may optionally be formulated in a standard form (e.g., a commercially available composition). In some such embodiments, the compositions comprising the alginate composition and the hepatotoxic agent are administered concomitantly.

In some of any one of the embodiments described herein, the alginate composition and hepatotoxic agent are administered via different routes of administration. For example, in some embodiments, the alginate composition is administered by oral administration, and the hepatotoxic agent is administered by intraperitoneal administration (e.g., wherein intraperitoneal administration is a standard route of administration for the agent) or by buccal administration, transdermal administration, transmucosal administration, inhalation, rectal administration, and/or intravenous injection (e.g., wherein such a route of administration is a standard route of administration for the agent). In some embodiments, the alginate composition is administered by intraperitoneal administration, and the hepatotoxic agent is administered by oral administration (e.g., wherein oral administration is a standard route of administration for the agent).

In some of any one of the embodiments described herein, the alginate composition and hepatotoxic agent are co-formulated within the same composition (i.e., as one composition). Pharmaceutical compositions comprising both alginate composition and hepatotoxic agent are described herein.

In some of any one of the embodiments described herein, the alginate composition and hepatotoxic agent, either co-formulated or formulated separately, are administered via the same route of administration. For example, in some embodiments, the alginate composition and hepatotoxic agent are administered by oral administration (e.g., wherein oral administration is a standard route of administration for the hepatotoxic agent), and in some embodiments, the alginate composition and hepatotoxic agent are administered by intraperitoneal administration (e.g., wherein intraperitoneal administration is a standard route of administration for the hepatotoxic agent).

In any aspect of embodiments of the invention described herein, an alginate according to any one of the embodiments described herein may be used in association with a hepatotoxic agent according to any of the embodiments described herein regarding a hepatotoxic agent, unless otherwise indicated.

In some of any one of the embodiments described herein, the alginate comprises an alginate which may be in a form of alginic acid (i.e., a protonated form) and/or in a form of an alginate salt (i.e., a non-protonated form). In some embodiments, the alginate includes both protonated and non-protonated carboxylic groups.

Examples of suitable alginate salts include, without limitation, a sodium salt, a potassium salt, a calcium salt, and a magnesium salt. In some embodiments, the alginate salt comprises at least one univalent cation, such as sodium and/or potassium. In exemplary embodiments, the alginate is in a form of a sodium salt.

Herein, a "sodium salt" of alginate refers to alginate which comprises at least 0.2 sodium ions per carboxylate group (of the alginate) bound to the alginate (e.g., by ionic bonds). In some of any one of the embodiments described herein, the alginate comprises at least 0.3 sodium ions per carboxylate group. In some embodiments, the alginate comprises at least 0.4 sodium ions per carboxylate group. In some embodiments, the alginate comprises at least 0.5 sodium ions per carboxylate group. In some embodiments, the alginate comprises at least 0.6 sodium ions per carboxylate group. In some embodiments, the alginate comprises at least 0.7 sodium ions per carboxylate group. In some embodiments, the alginate comprises at least 0.8 sodium ions per carboxylate group. In some embodiments, the alginate comprises at least 0.9 sodium ions per carboxylate group. In some embodiments, the alginate comprises at least 0.95 sodium ions per carboxylate group. In some embodiments, the alginate comprises at least 0.99 sodium ions per carboxylate group.

In some of any one of the embodiments described herein, a sodium salt is prepared by mixing an alginate in a solution containing sodium (e.g., a sodium chloride solution). In some embodiments, mixing is performed by homogenization (e.g., as exemplified herein). In exemplary embodiments, the sodium solution contains about 0.15 M sodium ions.

In some of any one of the embodiments described herein, the alginate comprises at least 0.2 univalent cations per carboxylate group (of the alginate) bound to the alginate (e.g., by ionic bonds). In some embodiments, the alginate comprises at least 0.3 univalent cations per carboxylate group. In some embodiments, the alginate comprises at least 0.4 univalent cations per carboxylate group. In some embodiments, the alginate comprises at least 0.5 univalent cations per carboxylate group. In some embodiments, the alginate comprises at least 0.6 univalent cations per carboxylate group. In some embodiments, the alginate comprises at least 0.7 univalent cations per carboxylate group. In some embodiments, the alginate comprises at least 0.8 univalent cations per carboxylate group. In some embodiments, the alginate comprises at least 0.9 univalent cations per carboxylate group. In some embodiments, the alginate comprises at least 0.95 univalent cations per carboxylate group. In some embodiments, the alginate comprises at least 0.99 univalent cations per carboxylate group.

In some of any one of the embodiments described herein, the alginate composition comprises alginate that is characterized by a molecular weight of up to 300 kDa. In some embodiments, the alginate is characterized by a molecular weight in a range of from 3 to 300 kDa. In some embodiments, the alginate is characterized by a molecular weight in a range of from 5 to 200 kDa. In some embodiments, the alginate is characterized by a molecular weight in a range of from 8 to 160 kDa. In some embodiments, the alginate is characterized by a molecular weight in a range of from 10 to 75 kDa. In some embodiments, the alginate is characterized by a molecular weight in a range of from 20 to 60 kDa. In some embodiments, the alginate is characterized by a molecular weight in a range of from 30 to 50 kDa.

In some of any one of the embodiments described herein, the alginate composition consists of an alginate as described herein and an aqueous carrier described herein, the alginate composition being characterized by a solution viscosity in a range of from 3 to 50 mPa*seconds, at a shear rate of 1 second$^{-1}$ and at a concentration of 2% weight/volume (20 grams per liter) in the aqueous carrier. In some embodiment, the solution viscosity is in a range of from 3 to 20 mPa*seconds. In some embodiment, the solution viscosity is in a range of from 5 to 20 mPa*seconds. In some embodiment, the solution viscosity is in a range of from 10 to 20 mPa*seconds. In some embodiment, the solution viscosity is in a range of from 5 to 50 mPa*seconds. In some embodiment, the solution viscosity is in a range of from 10 to 50 mPa*seconds. In exemplary embodiments, the solution viscosity is about 15.5 mPa*seconds.

It is to be understood that the phrase "at a concentration of 2%" does not indicate that the concentration of alginate in the alginate composition is necessarily 2%. Rather, the phrase means that a solution viscosity is determined for a composition consisting of the alginate (at a concentration of 2%) and the aqueous carrier, that is the composition for which solution viscosity is determined may differ from the alginate composition described herein only in the relative amount of the aqueous carrier.

Techniques for determining a molecular weight and/or a solution viscosity of alginate are exemplified herein. Additional techniques will be known by the skilled person.

The abovementioned ranges of alginate molecular weight and solution viscosity correspond to a relatively small molecular size of the alginate, including alginate known in the art as VLVG (very low viscosity high G alginate). As shown in the Examples herein, VLVG alginate exhibits more efficacy than do alginates characterized by larger molecular size.

Without being bound by any particular theory, it is believed that such relatively small molecular size facilitates diffusion of the alginate and transport in vivo, and that this enhances the therapeutic efficacy of the alginate composition. It is further believed that such relatively small molecular sizes are so small as to significantly alter the properties of alginate in the alginate composition which are believed to be play a role in the therapeutic efficacy of the alginate composition, for example, by inhibiting the ability of alginate to form a hydrogel.

In some of any one of the embodiments described herein, the alginate composition is a composition described in co-filed International Patent Application 29/017,846, which claims priority from U.S. Provisional Patent Application No. 61/747,328, the contents of which are incorporated herein by reference in their entirety. Such a composition comprises alginate, a source of sodium ions (e.g., sodium salt) and a carrier (e.g., as described herein). As described therein, homogenization of alginate with the sodium ions (e.g., in saline) alters the physical properties of alginate composition considerably, in such a manner as to significantly enhance dissolution and diffusion of the alginate.

In some of any one of the embodiments described herein, the alginate-containing composition (as described in the abovementioned International Patent Application) is characterized by at least one of the following properties:
  (i) A zeta potential weaker than −25 mV (i.e., closer to 0 mV), at a concentration of 0.5% (weight per volume) alginate in the abovementioned carrier;
  (ii) A diffusion coefficient of at least $10^{-8}$ cm$^2$/millisecond, at a concentration of 0.5% (weight per volume) alginate in the abovementioned carrier;
  (iii) A solution viscosity in a range of from 3 to 20 mPa*seconds, at a shear rate of 1 second$^{-1}$ and at a concentration of 2% weight/volume (20 grams per liter) in the carrier;
  (iv) A small angle X-ray scattering (SAXS) pattern characterized by an absence of a peak in scattering intensity in the interval 0.012<q<0.7 Å$^{-1}$; and
  (v) An absence of structures observable by transmission electron microscopy (e.g., cryogenic transmission electron microscopy) which are more than 5 nm in width.

Techniques for determining a diffusion coefficient, zeta potential, SAXS pattern, transmission electron microscopy image and/or a solution viscosity of alginate are exemplified therein. Additional techniques will be known by the skilled person. Values of diffusion coefficients, zeta potentials and solution viscosities refer to values at a temperature of 25° C.

In order to determine a presence or absence of structures by transmission electron microscopy, specimens are preferably vitrified (e.g., by rapid plunging into liquid ethane pre-cooled with liquid nitrogen) in a controlled-environment vitrification system, and examined using low-dose imaging, as exemplified herein, so as to prevent microstructural changes by ice crystallization and/or radiation damage. In addition, microscopy is preferably performed without heavy metal staining, so as to avoid structural changes due to interactions between alginate and heavy metal.

In some of any one of the embodiments described herein, the alginate in the composition is characterized by at least two of the aforementioned properties. In some embodiments, the alginate in the composition is characterized by at least 3 of the aforementioned properties. In some embodiments, the alginate in the composition is characterized by at least 4 of the aforementioned properties. In some embodiments, the alginate in the composition is characterized by all of the aforementioned properties.

In some of any one of the embodiments described herein, the composition is characterized by a diffusion coefficient of at least $10^{-8}$ cm$^2$/millisecond at a concentration of 0.5%, as described herein. In some embodiments, the diffusion coefficient is at least $2\times10^{-8}$ cm$^2$/millisecond. In some embodiments, the diffusion coefficient is at least $3\times10^{-8}$ cm$^2$/millisecond. In some embodiments, the diffusion coefficient is at least $4\times10^{-8}$ cm$^2$/millisecond. In some embodiments, the diffusion coefficient is at least $5\times10^{-8}$ cm$^2$/millisecond. In some embodiments, the diffusion coefficient is at least $6\times10^{-8}$ cm$^2$/millisecond. In some embodiments, the diffusion coefficient is at least $7\times10^{-8}$ cm$^2$/millisecond. In some embodiments, the diffusion coefficient is at least $8\times10^{-8}$ cm$^2$/millisecond. In some embodiments, the diffusion coefficient is at least $9\times10^{-8}$ cm$^2$/millisecond. In some embodiments, the diffusion coefficient is at least $10^{-7}$ cm$^2$/millisecond. In some embodiments, the diffusion coefficient is at least $2\times10^{-7}$ cm$^2$/millisecond. In some embodiments, the diffusion coefficient is at least $3\times10^{-7}$ cm$^2$/millisecond.

It is to be understood that the phrase "at a concentration of 0.5%", recited herein with respect to diffusion coefficients and zeta potentials, does not indicate that the concentration of alginate in the composition described herein is necessarily 0.5%. Similarly, the phrase "at a concentration of 2%", recited herein with respect to solution viscosities, does not indicate that the concentration of alginate in the composition described herein is necessarily 2%. Rather, the phrases mean that a diffusion coefficient, zeta potential and solution viscosity are determined for a composition consisting of the alginate (at a concentration of 2% or 0.5%) and the carrier (and a source of sodium ions), that is, the composition for which diffusion coefficient, zeta potential or solution viscosity is determined may differ from the composition of embodiments of the invention in the amount of the carrier relative to the alginate. Thus, for example, a diffusion coefficient and/or zeta potential may be characterized by measuring a composition as described herein after the composition has been diluted with carrier (with a source of sodium ions) to result in an alginate concentration of 0.5%, as exemplified herein.

Diffusion coefficients may be determined using dynamic light scattering measurement, by recording the real time fluctuations in the intensity of the scattered light. Equations for calculating a diffusion coefficient based on measurement of the intensity time correlation function as a function of the decay time, are described in the Examples section herein.

In some of any one of the embodiments described herein, the alginate composition is characterized by at least one of a zeta potential described herein and a diffusion coefficient described herein.

In some of any one of the embodiments described herein, the alginate composition is characterized by a zeta potential described herein.

In some of any one of the embodiments described herein, the composition is characterized by both a diffusion coefficient as described herein, and a zeta potential as described herein.

Herein and in the art, the phrase "zeta potential" refers to electric potential difference between a dispersion medium (e.g., a liquid medium of the composition described herein) and a stationary layer of fluid attached to a dispersed particle (e.g., alginate). As alginate is negatively charged (due to the presence of carboxylate groups), the zeta potential of alginate in the carrier is negative. Thus, a "weaker" zeta potential refers to a value closer to 0 mV (i.e., less negative).

In some of any one of the embodiments described herein, the zeta potential is weaker than −23 mV, under the abovementioned measurement conditions. In some embodiments, the zeta potential is weaker than −21 mV. In some embodiments, the zeta potential is weaker than −20 mV. In some embodiments, the zeta potential is weaker than −19 mV.

Without being bound by any particular theory, it is believed that a weak zeta potential (e.g., weaker than −25 mV) indicates a high degree of masking by sodium ions of the negative charge of alginate carboxylate groups, which in turn weakens intermolecular forces between alginate molecules.

In some of any one of the embodiments described herein, the zeta potential is at least −10 mV (i.e., −10 mV or a more negative value). In some embodiments, the zeta potential is at least −12.5 mV. In some embodiments, the zeta potential is at least −15 mV. In some embodiments, the zeta potential is in a range of from about −17.8 mV to about −21.2 mV. In some embodiments, the zeta potential is about −17.8 mV.

Without being bound by any particular theory, it is believed that a very weak zeta potential (e.g., weaker than −10 mV) indicates a high degree of instability, as there is little electrostatic forces to repel alginate molecules from one another.

Zeta potentials may be determined by analyzing experimentally measured electrophoretic mobility distributions using a standard theoretical model. Devices for performing the measurements and analysis include, for example, a Zeta Plus™ zeta potential analyzer (Brookhaven Instruments Corp., NY).

In some of any one of the embodiments described herein, the composition comprising alginate as described herein is characterized by a solution viscosity in a range of from 5 to 20 mPa*seconds, under the measurement conditions described herein. In some embodiment, the solution viscosity is in a range of from 10 to 20 mPa*seconds. In some embodiments, the solution viscosity is about 15.5 mPa*seconds.

Solution viscosity can be determined using commercially available stress-control rheometers (e.g., AR 2000 stress-control rheometer, TA Instruments). In exemplary embodiments, the rheometer is operated in the coneplate mode with a cone angle of 1° and a 60 mm diameter, as exemplified herein.

The phrase "absence of a peak in scattering intensity in the interval $0.012<q<0.7$ Å$^{-1}$" means that for the aforementioned range of values for the variable q, where q is defined as:

$$q = \frac{4\pi}{\lambda}\sin\theta$$

where 2θ is the scattering angle, and λ is the radiation wavelength (e.g., about 1.542 Å), there is no value of q for which the scattering intensity obtained by small angle X-ray scattering is greater than for slightly lower and higher values of q. Typically, in such a situation, the scattering intensity is simply correlated to the values of q, such that the highest scattering intensities are obtained for the highest values of q measured, as exemplified herein.

Small angle X-ray scattering measurements (e.g., utilizing Cu Kα radiation) may be performed at ambient temperature (e.g., 25° C.) using commercially available devices (e.g., SAXSLAB GANESHA 300-XL system). The 2D SAXS images are azimuthally averaged to produce one-dimensional profiles of intensity, I vs. q, using commercially available data analysis programs, as exemplified herein. The scattering spectra of the capillary and control composition (i.e., composition lacking alginate) are collected and subtracted from the corresponding composition data, to produce the above-described scattering intensity as a function of q.

In some of any one of the embodiments described herein, the alginate composition is characterized by a diffusion coefficient described herein and by a solution viscosity described herein.

In some of any one of the embodiments described herein, the alginate composition is characterized by a zeta potential described herein and by a solution viscosity described herein.

In some of any one of the embodiments described herein, the composition is characterized by a diffusion coefficient as described herein, a zeta potential as described herein, and by a solution viscosity described herein.

In some embodiments, the alginate composition is characterized by a diffusion coefficient described herein and by a scattering pattern described herein.

In some embodiments, the alginate composition is characterized by a zeta potential described herein and by a scattering pattern described herein.

In some embodiments, the composition is characterized by a diffusion coefficient as described herein, a zeta potential as described herein, and by a scattering pattern described herein.

In some embodiments, the alginate composition is characterized by a diffusion coefficient described herein and by an absence of observable structures more than 5 nm in width, as described herein.

In some embodiments, the alginate composition is characterized by a zeta potential described herein and by an absence of observable structures more than 5 nm in width, as described herein.

In some embodiments, the composition is characterized by a diffusion coefficient as described herein, a zeta potential as described herein, and by an absence of observable structures more than 5 nm in width, as described herein.

The alginate may be characterized by any ratio of mannuronic acid residues (M) to guluronic acid residues (G).

In some of any one of the embodiments described herein, mannuronic acid represents at least 5% of the residues. In some embodiments, mannuronic acid represents at least 10% of the residues. In some embodiments, mannuronic acid represents at least 20% of the residues. In some embodiments, mannuronic acid represents at least 30% of the residues. In some embodiments, mannuronic acid represents at least 45% of the residues. In some embodiments, mannuronic acid represents at least 50% of the residues. In some embodiments, mannuronic acid represents at least 60% of the residues. In some embodiments, mannuronic acid represents at least 70% of the residues. In some embodiments, mannuronic acid represents at least 80% of the residues. In some embodiments, mannuronic acid represents at least 90% of the residues. In some embodiments, mannuronic acid represents at least 95% of the residues.

In some of any one of the embodiments described herein, mannuronic acid represents from 25% to 65% of the residues, and guluronic acid represents from 35% to 75% of the residues.

In some of any one of the embodiments described herein, the alginate is cross-linked or partially cross-linked, for example, by cations (e.g., divalent or trivalent cations) such as calcium, copper, aluminum, magnesium, strontium, barium, tin, zinc and/or chromium ions, and/or by organic cations and/or cationic polymers. In some embodiments, the alginate is not cross-linked by molybdenum, vanadium, tungsten or chromium ions.

In some embodiments, the alginate is non-cross-linked (e.g., substantially free of cations other than univalent cations).

In some of any one of the embodiments described herein, the alginate is not silylated alginate.

In some of any one of the embodiments described herein, the alginate described herein is derived from brown algae. Suitable brown algae sources include, without limitation, *Laminaria hyperborea* and *Macrocystis pyrifera*.

Types of alginate suitable for use in the context of embodiments of the present invention are also described in International Patent Application WO 2009/069131, the contents of which are incorporated herein by reference.

According to any of the aspects described herein, the alginate composition and/or the hepatotoxic agent described herein can be administered either as alginate and/or hepatotoxic agent per se (e.g., alginate composition described herein consists of alginate per se and is administered as such), or as alginate and/or hepatotoxic agent as a part of a composition which further comprises a pharmaceutically acceptable carrier (e.g., the alginate composition described herein consists of alginate and a pharmaceutically acceptable carrier).

Hence, according to still another aspect of the present invention, there is provided a pharmaceutical composition, which comprises a therapeutically effective amount of a hepatotoxic agent and a therapeutically effective amount of an alginate composition, the alginate composition comprising a carrier which is a pharmaceutically acceptable carrier.

As used herein a "pharmaceutical composition" refers to a preparation of one or more active agents (e.g., alginate and/or hepatotoxic agent) as described herein, with other chemical components such as pharmaceutically acceptable and suitable carriers and excipients. The purpose of a pharmaceutical composition is to facilitate administration of a compound to an organism.

Herein, the term "pharmaceutically acceptable carrier" refers to a carrier or a diluent that does not cause significant irritation to an organism and does not abrogate the biological activity and properties of the administered compound. Examples, without limitations, of pharmaceutically acceptable carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

It is to be understood that an alginate composition may consist of an alginate and a pharmaceutically acceptable carrier (as described herein), wherein the carrier is a solution containing a hepatotoxic agent (as described herein), and that such an alginate composition is, in itself, a pharmaceutical composition such as described herein. However, for convenience and simplicity, such a pharmaceutical composition is generally described herein as a combination of a hepatotoxic agent and an alginate composition, that is, the hepatotoxic agent is not considered as being a component of the alginate composition.

It is to be further understood that a combination of a hepatotoxic agent and an alginate composition comprising alginate and a carrier, as described herein, does not indicate that the carrier is necessarily contacted with the alginate (to form an alginate composition) prior to being contacted with the hepatotoxic agent. Rather, the components of the alginate composition (carrier and alginate) and the hepatotoxic agent may be combined in any order.

In some embodiments wherein the alginate composition and/or pharmaceutical composition described herein comprises a liquid carrier (e.g., an aqueous carrier), the composition comprises alginate at a concentration in a range of from 0.4% to 10% (w/v). In some embodiments, the concentration is in a range of from 1% to 4% (w/v). In exemplary embodiments, the concentration is about 2% (w/v).

Techniques for formulation and administration of drugs may be found in "Remington's Pharmaceutical Sciences" Mack Publishing Co., Easton, Pa., latest edition, which is incorporated herein by reference.

Pharmaceutical compositions of embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention thus may be formulated in conventional manner using one or more pharmaceutically acceptable carriers comprising excipients and auxiliaries, which facilitate processing of the alginate and/or hepatotoxic agent into preparations which, can be used pharmaceutically. Proper formulation is dependent upon the route of administration chosen.

In some embodiments, the alginate composition and/or hepatotoxic agent described herein are formulated for systemic administration.

In some embodiments, the alginate composition and/or hepatotoxic agent described herein are formulated for intraperitoneal administration (e.g., intraperitoneal injection).

For injection, the alginate and/or hepatotoxic agent described herein may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

As exemplified herein, oral administration is a particularly effective and convenient route for administering an alginate composition.

For oral administration, the alginate composition and/or hepatotoxic agent described herein can be formulated readily by combining the alginate and/or hepatotoxic agent with pharmaceutically acceptable carriers well known in the art. Such carriers enable the alginate and/or hepatotoxic agent described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone or agar. It is to be appreciated that alginate may also be an effective disintegrating agent.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of alginate and/or hepatotoxic agent doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the alginate and/or hepatotoxic agent described herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the alginate composition and/or hepatotoxic agent described herein may be conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the alginate composition and/or hepatotoxic agent described herein and a suitable powder base such as, but not limited to, lactose or starch.

The alginate composition and/or hepatotoxic agent described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing to agents.

The phrase "unit dosage form", as used herein, describes physically discrete units, each unit containing a predetermined quantity of active ingredients (e.g., an alginate and/or hepatotoxic agent as described herein) calculated to produce the desired effect, in association with at least one pharmaceutically acceptable carrier, diluent, excipient, or combination thereof.

Pharmaceutical compositions for parenteral administration include aqueous solutions of the alginate and/or hepatotoxic agent described herein in water-soluble form. Additionally, suspensions of the alginate and/or hepatotoxic agent described herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the alginate and/or hepatotoxic agent described herein to allow for the preparation of highly concentrated solutions.

Alternatively, the alginate composition and/or hepatotoxic agent described herein may be in powder form for constitution with a suitable vehicle, e.g., sterile, pyrogen-free water or saline, before use.

The alginate composition and/or hepatotoxic agent described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount of alginate composition and/or hepatotoxic agent described herein is an amount effective to prevent, alleviate or ameliorate symptoms of liver damage and/or disease treatable by hepatotoxic agent, and/or prolong the survival of the subject being treated.

Determination of a therapeutically effective amount of alginate composition and/or hepatotoxic agent described herein is well within the capability of those skilled in the art, especially in light of the detailed disclosure provided herein, as well as knowledge in the art regarding dosage of hepatotoxic agents.

For any alginate composition and/or hepatotoxic agent described herein, the therapeutically effective amount or dose can be estimated initially from activity assays in animals (e.g., as exemplified herein). For example, a dose can be formulated in animal models to achieve a circulating concentration range that includes the $IC_{50}$ as determined by activity assays (e.g., the concentration of the alginate, which achieves a half-maximal reduction of liver damage, as quantified according to assays known in the art (e.g., assays exemplified herein). Such information can be used to more accurately determine useful doses in humans.

A therapeutically effective amount for the alginate in a composition may range from about 8 mg/kg body weight to about 3,200 mg/kg body weight. In some embodiments, the therapeutically effective amount for the alginate is from about 16 mg/kg body weight to about 3,200 mg/kg body weight. In some embodiments, the therapeutically effective amount for the alginate is more than 40 mg/kg body weight. In some embodiments, the therapeutically effective amount for the alginate is at least about 80 mg/kg body weight. As is demonstrated in the Examples section that follows, an amount of an alginate of 100 mg/kg or higher was shown to exhibit a more potent protective effect in mice than 50 mg/kg.

Toxicity and therapeutic efficacy of the alginate composition and/or hepatotoxicity described herein can be determined based on prior knowledge in the art regarding such agents and/or by standard pharmaceutical procedures in experimental animals, e.g., by determining the $EC_{50}$, the $IC_{50}$ and the $LD_{50}$ (lethal dose causing death in 50% of the tested animals). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each agent, but can be estimated from in vitro data. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release or delayed release formulation of a composition described hereinabove, with course of treatment lasting from several hours to several weeks or until cure is effected or diminution of the disease state is achieved.

In some embodiments of any of the aspects described herein, administration is effected using a composition formulated as a slow release or delayed release composition, designed to achieve maximal overlap between exposure of the liver to the effects of the alginate and exposure of the liver to the hepatotoxic agent. In order to maximize such overlap, either the alginate composition, the hepatotoxic agent, or both, may be formulated for slow release and/or delayed release, depending on the relative pharmacokinetics of the alginate and hepatotoxic agent.

For example, in some embodiments, a hepatotoxic drug is formulated for slow release and/or delayed release (e.g., a standard commercially available formulation of the drug), and an alginate composition for co-administration with the drug is formulated for a slow release and/or delayed release with similar release kinetics. Alternatively, a hepatotoxic drug is formulated for delayed release (e.g., a standard commercially available formulation of the drug), and an alginate composition for co-administration with the drug is co-administered prior to, concomitant with or shortly after the hepatotoxic agent is released (which is the exposure of the subject to the hepatotoxic agent).

Techniques for preparing slow release formulations are known in the art, including suitable coatings for solid compositions which release the coated compositions according to a pre-determined time profile, and suitable capsules which release liquid compositions after a pre-determined period of time.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the alginate composition and/or hepatotoxic agent described herein. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an alginate composition and/or hepatotoxic agent described herein formulated in a compatible pharmaceutical carrier may also be prepared, placed in an appropriate container, and labeled for treatment of an indicated condition or diagnosis, as is detailed hereinabove (e.g., treating liver damage, reducing or preventing a liver damage caused by at least one identified hepatotoxic agent, treating a condition treatable by the hepatotoxic agent).

Thus, according to some embodiments of any aspect described herein, the alginate composition and/or hepatotoxic agent described herein, for example, in a form of a composition described herein, are packaged in a packaging material and identified in print, in or on the packaging material, for use in the treatment of a condition described herein (e.g., alginate composition identified for protecting against liver damage, for treating liver damage and/or for reducing or preventing a liver damage caused by at least one identified hepatotoxic agent; composition comprising alginate and hepatotoxic agent identified for treating a condition treatable by the hepatotoxic agent in the composition).

The co-formulations described herein of a hepatotoxic agent with an alginate composition are considerably superior to current formulations of hepatotoxic agents, in view of the hepatoprotection provided by the alginate. The co-formulations described herein may therefore be used without required warnings against the risk of liver damage (or with less stringent warnings) and/or without required monitoring of liver function (or with less frequent monitoring) in a subject being administered the co-formulation, in contrast to current formulations of hepatotoxic agents.

It is expected that during the life of a patent maturing from this application many relevant hepatotoxic agents will be developed and/or newly identified and the scope of the term "hepatotoxic agent" is intended to include all such new agents a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:

Alginates (VLVG and LVG) were obtained from Nova-Matrix. VLVG refers to Very Low Viscosity (high) G alginate, as designated by the manufacturer. LVG refers to Low Viscosity (high) G alginate, as designated by the manufacturer. LVG alginate with different molecular weight are referred to herein as LVG54 and LVG150, wherein the numbers are those reported by the manufacturer for solution viscosity of the product for 1% (w/v) solutions.

Hyaluronan (sodium salt; ~400 kDa; from *Streptococcus equinus*) was obtained from Sigma.

Concanavalin A (Con A) was obtained from MP Biomedicals.

Paracetamol syrup (Tiptipot® syrup) and the vehicle (paracetamol-free) for the syrup were obtained from CTS (Israel).

Preparation of Polysaccharide Solutions:

Polysaccharides (e.g., alginate) were dissolved in saline (0.15 M NaCl in water), and mixed intensively with a homogenizer (28,000 rotations per minute, for 3 minutes). All of the alginate samples included alginate at a concentration of 2% (w/v). All samples were sterilized by filtration through a 0.2 µm nylon membrane. The solutions were maintained at a temperature of 4° C. until use, and appeared clear by eye.

Animals:

Male C57BL/6 (B6) mice (11-12 weeks old) were purchased from Harlan Laboratories (Jerusalem, Israel). All mice were maintained in specific pathogen-free conditions. Mice were maintained in the Animal Core of the Hadassah-Hebrew University Medical School. All mice were administered standard laboratory chow and water ad libitum and kept in a 12-hour light/dark cycle.

Rheological Characterization of the Polysaccharide Solutions:

The viscosity of the polysaccharide solutions was tested on an AR 2000 stress-control rheometer (TA Instruments), operated in the coneplate mode with a cone angle of 1° and a 60 mm diameter. The apparent viscosities (mPa*seconds) of the solutions were tested at a shear rate of 1 seconds$^{-1}$. The measuring device was equipped with a temperature control unit (Peltier plate, $^{\pm}0.05°$ C.) operated at 25° C.

Determination of Polysaccharide Molecular Weight:

Polysaccharide molecular weights were determined by gel permeation chromatography-multiangle laser light scattering (GPC-MALLS). Samples were separated on a chromatographic system comprising a Waters 606 pump followed by two PSS Suprema gel permeation columns connected in a series (column description: dimensions 300×8 mm$^2$, particle size 10 mm, porosity of 3000 and 10,000 angstrom). The flow rate was 0.5 ml/minute. The columns were kept at a constant temperature of 25° C. inside a Techlab K-4 controlled oven. The chromatographic system was attached to a Dawn DSP (Wyatt Technology) multiangle laser light scattering (MALLS) photometer equipped with a He/Ne laser working at 632.8 nm, a K5 refraction cell and 18 detectors at angles of 14-163°.

Concentration was monitored by a calibrated interferometric refractometer Optilab DSP (Wyatt Technology). Data processing and molar mass calculation were performed with Wyatt ASTRA software version 4.7. Each sample was injected three times to ensure reproducibility. The dn/dc of the alginate, measured with the Optilab DSP, controlled by Wyatt dn/dc software, was found to be 0.155 ml/gram (aqueous buffer).

Aqueous buffer solutions were prepared from ultrapure water (0.055 µs/cm, USF Seral Purelab RO75, followed by USF Seral Purelab UV) supplemented with 0.1 M NaNO$_3$, 0.02% (w/v) NaN$_3$ and 10 mM imidazole. The buffer was titrated with NaNO$_3$ to a pH of 7.0 and filtered through a 0.1 µm VacuCap® 60 filter (Gelman Sciences).

Alanine Aminotransferase (ALT) Assays:

Serum activities of alanine aminotransferase (ALT) was carried out after 1:10 dilutions, using a Reflovet® Plus clinical chemistry analyzer (Roche Diagnostics).

IL-6 Assays:

Serum levels of IL-6 were determined by "sandwich" ELISA, using a Quantikine® assay kit (R&D Systems), according to the manufacturer's instructions. Sera from mice were frozen until ELISA analysis.

Paracetamol Intoxication Mouse Model:

Male C57BL/6 (B6) mice (11-12 weeks old) were orally administered Tiptipot® paracetamol (acetaminophen, N-acetyl-p-aminophenol, APAP) syrup, after an overnight fast. The paracetamol dosages were 160 mg/kg (approximately 4 mg) or 320 mg/kg (approximately 8 mg) in other examples. The syrup was always diluted with saline to yield a total volume of 350 µl per mouse. Paracetamol was administered in the morning and food was put back to the cages 2 hours later. Mice were sacrificed 24 hours after paracetamol administration.

In the preventive model, alginate solutions (50, 100 or 200 µl per mouse) were administered per os or i.p. prior to administration of 160 mg/kg (approximately 4 mg) or 320 mg/kg (approximately 8 mg) paracetamol. In the therapeutic model, alginate solutions were administered with 160 mg/kg (approximately 4 mg) paracetamol (by being mixed with the paracetamol) or shortly thereafter.

Control mice were administered only with paracetamol syrup diluted with saline, as described hereinabove. In some experiments control mice were orally administered with the vehicle for the Tiptipot® paracetamol syrup, which was identical to the paracetamol syrup except for being paracetamol-free.

In some experiments paracetamol levels in the blood were determined 30 or 60 min after paracetamol administration, by taking 20 µl of blood from the tail vein of all mice. Paracetamol levels were measured by using a clinical kit based on fluorescence polarization immunoassay (FPIA, AxSYM acetaminophen assay (Abbott), obtained from Hex Medical Ltd., Israel). Serum activities of ALT and cytokines were determined as described herein.

After mice were sacrificed, a portion of each excised liver was fixed in 10% formalin and was then embedded in paraffin, sectioned (specimens of 5 µm) and stained with hematoxylin & eosin (H&E) or with IgG staining for detection of necrosis, nitrotyrosine and/or Ki-67. Briefly, necrosis staining was as follows: sections were first de-paraffinized and then were incubated with rabbit polyclonal IgG. Sections were then incubated with secondary antibody using the MACH 3 Rabbit HRP Polymer Detection and then dehydrated, cleared and mounted in synthetic resin. For color detection, DAB (3,3'-diaminobenzidine) was applied, followed by counterstaining Quantification of necrosis was carried out by the Ariol SL-50 system (Applied Imaging) on microscope slides. Nitrotyrosine and Ki-67 immunostaining staining was performed similarly, using a rabbit polyclonal anti-nitrotyrosine antibody (Abcam) or an anti-Ki-67 antibody (DAKO).

Weight changes were monitored by weighing all the mice on the fasting day, the following morning, just before paracetamol administration (Day 1) and on the following day before sacrifice (Day 2).

Example 1

Effect of Alginate on Paracetamol Hepatotoxicity (Preventive Model)

Aqueous solutions of 2% alginate (w/v) were prepared by homogenization in saline, as described in the Materials and Methods section, from the following types of alginate:

VLVG (solution viscosity 15.5 mPa*seconds, molecular weight 30-50 kDa);

LVG54 (solution viscosity 269 mPa*seconds, molecular weight 100 kDa); and

LVG150 (solution viscosity 879 mPa*seconds, molecular weight 156 kDa).

Solution viscosity and molecular weight were characterized as described hereinabove.

The effect of alginate on paracetamol hepatotoxicity was investigated in a mouse model, as described in the Materials and Methods section.

To this end, 200 µl of a 2% solution of VLVG alginate was administered per os 30 minutes prior to intoxication with 4 mg paracetamol. Paracetamol intoxication was evaluated by measuring levels of ALT and IL-6, by measuring the weight loss typical of paracetamol intoxication, and by examining necrosis by IgG staining, according to procedures described in the Materials and Methods section.

Figure 1:
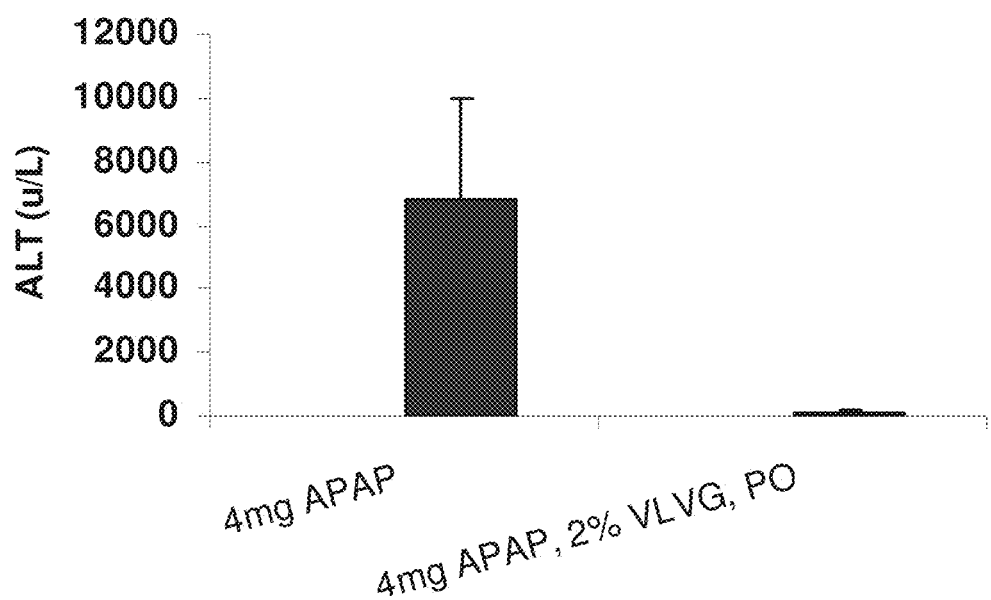

As shown in FIG. 1, the orally administered VLVG alginate dramatically reduced serum ALT levels in mice 24 hours after paracetamol administration, from 6,785±3,230 units per liter to 109±54 units per liter.

In addition, the orally administered VLVG alginate reduced serum IL-6 levels from 119.6±66.6 pg/ml to 45.6±33.3 pg/ml (p=0.05).

In addition, as shown in Table 2 below, the orally administered VLVG alginate reversed the weight loss caused by paracetamol intoxication between Day 1 (the day of intoxication) and Day 2 (the following day).

In addition, as shown in FIGS. 2A and 2B, the orally administered VLVG alginate reduced the degree of necrosis in the liver of paracetamol intoxicated mice.

TABLE 2

Effect of 4 mg paracetamol and VLVG alginate on body weight

| Group | Weight ratio (Day 2 vs. Day 1) | Change in weight from Day 1 to Day 2 (mg) |
|---|---|---|
| 4 mg paracetamol alone | 99% | −0.15 |
| 4 mg paracetamol + VLVG alginate (2% w/v, per os) | 105% | 1.17 | p < 0.0001 for change in weight

In order to assess the effect of alginate dosage on liver damage caused by paracetamol, the above experiment was repeated so as to compare the effects of 50, 100 and 200 µl of a 2% solution of VLVG alginate, which correspond to doses of 1 mg, 2 mg and 4 mg of VLVG alginate, respectively.

As shown in FIG. 3, 100 µl (2 mg alginate) and 200 µl (4 mg alginate) of the orally administered VLVG alginate solution dramatically reduced serum ALT levels in mice 24 hours after paracetamol administration, from 15133±1283 units per liter to 149±28 units per liter and 62±15 (200 µl) units per liter, respectively, whereas 50 pi (1 mg alginate) of the orally administered VLVG alginate only moderately reduced serum ALT levels, from 15133±1283 units per liter to 10813±2253 units per liter.

The effects of different dosages of alginate on liver damage caused by paracetamol were also assessed by staining for nitrotyrosine (a marker of oxidative stress associated with peroxynitrite formation due to increased nitric oxide production following liver injury) and Ki-67 (a marker of cell proliferation), according to procedures described in the Materials and Methods section. Paracetamol toxicity develops only after the onset of oxidative stress and mitochondrial dysfunction, and preventing these phenomena protects against paracetamol toxicity.

As shown in FIG. 4, treatment with 4 mg paracetamol resulted in extensive centrilobular nitrotyrosine staining, which was limited by 50 µl of 2% VLVG solution, and which was abolished by 200 µl of 2% VLVG solution.

As shown in FIG. 5, treatment with 4 mg paracetamol resulted in widespread cell proliferation in the liver, which was limited to certain areas by 50 µl of 2% VLVG solution, and which was abolished by 200 µl of 2% VLVG solution.

These results indicate that VLVG reduces oxidative stress and cell proliferation associated with paracetamol hepatotoxicity, and confirm that doses above 50 µl of 2% VLVG solution (1 mg alginate) can effectively prevent development of adverse effects associated with paracetamol hepatotoxicity.

Paracetamol is absorbed rapidly into the blood stream, reaching peak serum values in about 1-3 hours. In order to ascertain whether the protective effect is mediated by changes in paracetamol absorption, paracetamol levels in the blood were determined after administration of paracetamol.

As shown in FIG. 6, neither 100 µl nor 200 µl of the orally administered VLVG alginate solution exhibited any statistically significant effect on paracetamol levels in the blood 1, 4 or 24 hours after administration of paracetamol.

Similarly, when paracetamol levels in the blood were determined 30 minutes after administration of paracetamol, the paracetamol levels with and without administration of 200 µl of VLVG alginate solution were essentially identical: 67.72±40.55 µg/ml with VLVG alginate administration and 65.07±43.17 µg/ml without VLVG alginate.

These results indicate that the alginate does not affect paracetamol absorption, and that the protective effects of alginate are not mediated by changes in paracetamol absorption.

In order to further assess the effect of alginate on liver damage caused by paracetamol, the above experiment was repeated so as to compare the effect of orally administered VLVG alginate (200 µl of a 2% solution) with that of intraperitoneally administered VLVG alginate and with orally administered LVG54 and LVG150 alginate (200 µl of a 2% solution). Liver damage was evaluated by measuring ALT levels and body weight. Each treatment group included 4 mice.

As shown in FIG. 7, intraperitoneally administered VLVG alginate, orally administered VLVG alginate, LVG54 alginate and LVG150 alginate each reduced serum ALT levels in mice 24 hours after paracetamol administration. Furthermore, VLVG alginate was more effective than LVG54 and LVG150 alginate at reducing ALT levels, and orally administered VLVG alginate was more effective than intraperitoneally administered VLVG alginate. ALT levels were 13,250±2,415 units/liter 24 hours after paracetamol administration alone, and were reduced to 1,987±1,316 units/liter following i.p. administration of VLVG alginate, to 202±159 units/liter following oral administration of VLVG alginate, to 3,525±3,938 units/liter following oral administration of LVG54 alginate, and to 6,504±4,277 units/liter following oral administration of LVG150 alginate.

In addition, as shown in Table 3 below, intraperitoneally administered VLVG alginate, orally administered VLVG alginate, LVG54 alginate and LVG150 alginate each reversed the weight loss caused by paracetamol intoxication between Day 1 (the day of intoxication) and Day 2 (the following day).

TABLE 3

Effect of 4 mg paracetamol and alginate on body weight

| Group | Weight ratio (Day 2 vs. Day 1) | Change in weight from Day 1 to Day 2 (mg) |
| --- | --- | --- |
| 4 mg paracetamol alone | 96% | −1.05 |
| 4 mg paracetamol + VLVG alginate (2% w/v, i.p.) | 102% | 0.5 |
| 4 mg paracetamol + VLVG alginate (2% w/v, per os) | 101% | 2.1 |
| 4 mg paracetamol + LVG54 alginate (2% w/v, per os) | 108% | 2.08 |
| 4 mg paracetamol + LVG150 alginate (2% w/v, per os) | 103% | 0.8 |

The above results indicate that alginate can be administered by various routes to prevent liver damage caused by drug hepatotoxicity, but that oral administration of alginate is particularly effective for preventing liver damage caused by drug hepatotoxicity. The results further indicate that VLVG alginate is more effective against liver damage than alginates characterized by different molecular weights and viscosities.

In order to assess the ability of alginate to protect against liver damage caused by higher doses of paracetamol, the above experiments were repeated using doses of 8 mg paracetamol (a sub-lethal dose) instead of 4 mg. Paracetamol intoxication was evaluated by measuring levels of ALT and IL-6, and by measuring body weight. This experiment was performed twice, once with administration of a vehicle as a control (as described in the Materials and Methods section), and once without.

In one experiment, as shown in FIG. 8, VLVG alginate reduced serum ALT levels in mice 24 hours after administration of 8 mg paracetamol, from 21,743±5,790 units/liter to 10,903±4,798 units per liter.

In addition, the orally administered VLVG alginate reduced serum IL-6 levels from 91.65±28.9 pg/ml to 43.17±15.42 pg/ml ($p<0.005$).

In addition, as shown in Table 4 below, the orally administered VLVG alginate reversed the weight loss caused by paracetamol intoxication between Day 1 (the day of intoxication) and Day 2 (the following day).

TABLE 4

Effect of 8 mg paracetamol and VLVG alginate on body weight

| Group | Weight ratio (Day 2 vs. Day 1) | Change in weight from Day 1 to Day 2 (mg) |
| --- | --- | --- |
| 8 mg paracetamol alone | 99% | −0.17 |
| 8 mg paracetamol + VLVG alginate (2% w/v, per os) | 110% | 2.42 |

In the second experiment, as shown in FIG. 9, VLVG alginate reduced serum ALT levels in mice 24 hours after administration of 8 mg paracetamol, from 25,520±3,068 units/liter to 11,845±7,025 units per liter, whereas only 28±1 units/liter ALT was detected in serum when the vehicle was administered instead of paracetamol.

In addition, the orally administered VLVG alginate reduced serum IL-6 levels from 247.0±234 pg/ml to 84.4±25 pg/ml, whereas only 18.1±1.5 pg/ml IL-6 was detected in serum when the vehicle was administered instead of paracetamol.

In addition, as shown in Table 5 below, the orally administered VLVG alginate reversed the weight loss caused by paracetamol intoxication between Day 1 (the day of intoxication) and Day 2 (the following day).

TABLE 5

Effect of 8 mg paracetamol and VLVG alginate on body weight

| Group | Weight ratio (Day 2 vs. Day 1) | Change in weight from Day 1 to Day 2 (mg) |
|---|---|---|
| Syrup vehicle | 106% | 1.6 |
| 8 mg paracetamol alone | 99% | −0.3 |
| 8 mg paracetamol + VLVG alginate (2% w/v, per os) | 102% | 0.4 |

In addition, paracetamol levels in the blood were determined 30 minutes after administration of 8 mg paracetamol (or vehicle). The paracetamol levels with and without administration of VLVG alginate were essentially identical: 169.9±100.7 μg/ml with VLVG alginate administration and 153.4±99.8 μg/ml without VLVG alginate. In contrast, only 5.9±3.7 μg/ml paracetamol was detected when the vehicle was administered, which corresponds to the background signal for the assay kit.

These results indicate that alginate protects against relatively high doses of paracetamol, and that the protective effects of alginate are not mediated by changes in paracetamol absorption.

Example 2

Effect of Alginate on Paracetamol Hepatotoxicity (Therapeutic Model)

In view of the results presented in Example 1, which show a strong protective effect of alginate when administered prior to administration of paracetamol (a preventive model), the effect of alginate on paracetamol hepatotoxicity was investigated in a therapeutic model, in which alginate was administered concurrently with, or subsequent to, administration of paracetamol, as described in the Materials and Methods section.

To this end, a 2% solution of VLVG alginate was prepared as described hereinabove, and administered per os at a volume of 200 μl 30 or 60 minutes after intoxication with 4 mg paracetamol. Paracetamol intoxication was evaluated by measuring levels of ALT and IL-6, and by measuring body weight, as described hereinabove.

As shown in FIG. 10, VLVG alginate administered 30 minutes after paracetamol administration dramatically reduced serum ALT levels in mice 24 hours later, whereas VLVG alginate administered 60 minutes after paracetamol administration did not reduce serum ALT levels. Serum ALT levels were 1,025±1,310 units/liter when VLVG alginate was administered 30 minutes after paracetamol, 10,020±5,031 units/liter when VLVG alginate was administered 60 minutes after paracetamol, and 6,393±7,304 units/liter when paracetamol was administered without alginate.

In addition, VLVG alginate administered 30 minutes after paracetamol reduced serum IL-6 levels from 248.8±98.4 pg/ml to 63.4±42.5 pg/ml. In contrast, when VLVG alginate was administered 60 minutes after paracetamol, serum IL-6 levels were 131.1±52.4 pg/ml.

In addition, as shown in Table 6 below, VLVG alginate administered 30 minutes after paracetamol reversed the weight loss caused by paracetamol intoxication, whereas VLVG alginate administered 60 minutes after paracetamol did not.

TABLE 6

Effect of administration time of VLVG alginate on body weight

| Group | Weight ratio (Day 2 vs. Day 1) | Change in weight from Day 1 to Day 2 (mg) |
|---|---|---|
| 4 mg paracetamol alone | 94% | −1.5 |
| 4 mg paracetamol + VLVG alginate after 30 minutes | 104% | 1.03 |
| 4 mg paracetamol + VLVG alginate after 60 minutes | 98% | −0.43 |

The above experiment was repeated using VLVG alginate mixed with the paracetamol and co-administered.

As shown in FIG. 11, VLVG alginate dramatically reduced serum ALT levels in mice 24 hours later, whether administered 30 minutes after paracetamol or to when administered mixed with paracetamol, although the protective effect of the VLVG alginate was somewhat stronger when administered after paracetamol. Serum ALT levels were 124±93 units/liter when VLVG alginate was administered 30 minutes after paracetamol, 902±1,520 units/liter when VLVG alginate was mixed with paracetamol, and 6,734±3,783 units/liter when paracetamol was administered without alginate.

In addition, VLVG alginate reduced serum IL-6 levels in mice 24 hours later, whether administered 30 minutes after paracetamol or when administered mixed with paracetamol. VLVG alginate administered 30 minutes after paracetamol reduced serum IL-6 levels from 164.1±85.3 pg/ml to 58.9±31.8 pg/ml, while VLVG alginate mixed with paracetamol similarly reduced serum IL-6 levels to 58.9±38.7 pg/ml.

In addition, as shown in Table 7 below, VLVG alginate reversed the weight loss caused by paracetamol intoxication, whether administered 30 minutes after paracetamol or when administered mixed with paracetamol.

TABLE 7

Effect of administration time of VLVG alginate on body weight

| Group | Weight ratio (Day 2 vs. Day 1) | Change in weight from Day 1 to Day 2 (mg) |
|---|---|---|
| 4 mg paracetamol alone | 98% | −0.52 |
| 4 mg paracetamol + VLVG alginate after 30 minutes | 102% | 0.52 |
| 4 mg paracetamol mixed with VLVG alginate | 102% | 0.56 |

These results indicate that alginate exhibits a protective effect against drug hepatotoxicity, when administered prior to or concurrently with a hepatotoxic drug, or when administered less than 60 minutes after administration of the drug.

Example 3

Biodistribution of Alginate

The biodistribution of alginate was determined using immunohistochemical staining for biotin-labeled alginate.

VLVG alginate was labeled with biotin via carbodiimide chemistry, using procedures as described in Freeman et al.

[*Biomaterials* 29:3260-3268 (2008)]. No more than 3% of uronic acid residues were modified, so the biotin-labeled alginate was quite similar to the non-labeled alginate. A solution of 2% biotinylated VLVG alginate was administered to mice intraperitoneally (200 μl per mouse), and the mice were sacrificed after 48 hours. The liver, spleen, colon or other tissue were then harvested and fixed in 10% formalin and were then embedded in paraffin and sectioned (specimens of 5 μm). For biotin detection, slides were first de-paraffinized, followed by addition of target retrieval solution and then blocking by peroxidase blocker (DAKO). After incubations and rinsing, Streptavidin-peroxidase (DAKO) was applied. For color detection, DAB (3,3'-diaminobenzidine) and chromogen substrate were applied. The procedure was ended by counterstaining and cover slip mounting.

As shown in FIG. 12, intraperitoneally administered VLVG alginate appeared in the liver parenchyma, as determined by immunohistochemical staining.

Biotinylated VLVG alginate was then again administered intraperitoneally to mice, and the presence of VLVG alginate in various tissues was examined.

As shown in FIGS. 13A and 13B, intraperitoneally administered VLVG alginate appeared in the liver and pancreas of mice (FIG. 13B), but not in the spleen or colon of mice (FIG. 13A).

These results indicate that therapeutically effective amounts of alginate can infiltrate organs such as liver and pancreas, following systemic administration.

Example 4

Treatment by Co-Administration of Alginate and a Hepatotoxic Drug

A subject afflicted by a medical condition (e.g., a headache, an autoimmune disease, epilepsy) treatable by a hepatotoxic drug (e.g., paracetamol for treating a headache, methotrexate for treating an autoimmune disease, carbamazepine for treating epilepsy) is co-administered the hepatotoxic drug in combination with alginate. Co-administration is effected by administering the alginate during a time period ranging from 100 minutes prior to administration of the hepatotoxic drug to 50 minutes after administration of the hepatotoxic drug. The hepatotoxic drug is administered according to an accepted regimen for treating the medical condition, and the alginate is administered in a dose sufficient to prevent or reduce liver damage caused by the administered dosage of hepatotoxic drug.

The alginate is administered separately from the hepatotoxic drug (e.g., in the form of tablets, capsules or a syrup), or the alginate is co-formulated with the hepatotoxic drug in a form suitable for administration of the drug (e.g., in the form of tablets, capsules or a syrup).

The subject is optionally monitored for signs of liver damage according to a standard technique (e.g., by serum liver enzyme assay), and the dose of alginate is optionally increased if signs of liver damage appear.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition comprising a therapeutically effective amount of a hepatotoxic agent and a therapeutically effective amount of an alginate composition, said alginate composition comprising a pharmaceutically acceptable carrier, wherein said hepatotoxic agent is paracetamol, and said alginate composition comprises alginate characterized by a molecular weight in a range of from 10 to 75 kDa.

2. The composition of claim 1, being for treating a medical condition treatable by said hepatotoxic agent.

3. The composition of claim 1, wherein the alginate composition is for reducing or preventing a liver damage caused by said hepatotoxic agent.

4. The composition of claim 1, being a unit dosage form.

5. The composition of claim 1, wherein said carrier is an aqueous carrier.

6. The composition of claim 5, wherein said alginate composition is characterized by a solution viscosity in a range of from 3 to 50 mPa*seconds, at a shear rate of 1 second$^{-1}$ and at a concentration of 2% (w/v) alginate in said aqueous carrier.

7. The composition of claim 1, wherein said alginate composition comprises alginate at a concentration in a range of from 0.4% to 10% (w/v).

8. The composition of claim 1, wherein said alginate composition comprises alginate in a form of a sodium salt.

9. The composition of claim 1, being formulated for systemic administration.

10. The composition of claim 1, being formulated for oral administration.

11. The composition of claim 1, being formulated for intraperitoneal administration.

12. A method of reducing a liver damage caused by a hepatotoxic agent, the method comprising administering to a subject exposed to said hepatotoxic agent a therapeutically effective amount of an alginate composition, said administering being effected prior to, concomitant with, or shortly after exposure to said hepatotoxic agent, thereby reducing liver damage, wherein said hepatotoxic agent is paracetamol, said alginate composition comprises alginate characterized by a molecular weight in a range of from 10 to 75 kDa, and administration of said alginate composition is effected by oral administration.

13. The method of claim 12, wherein said administering is effected up to 50 minutes after exposure to said hepatotoxic agent.

14. The method of claim 12, wherein said administering is effected during a time period ranging from 100 minutes prior to exposure to said hepatotoxic agent to 50 minutes subsequent to exposure to said hepatotoxic agent.

15. A method of ameliorating the symptoms of a medical condition treatable by a hepatotoxic agent in a subject in need thereof, the method comprising co-administering to the subject a therapeutically effective amount of said hepatotoxic agent and a therapeutically effective amount of an alginate composition, said co-administering being effected such that said alginate composition is administered to the subject during a time period ranging from 100 minutes prior to administration of said hepatotoxic agent to 50 minutes subsequent to administration of said hepatotoxic agent, thereby ameliorating the symptoms of the medical condition, wherein said hepatotoxic agent is paracetamol, said medical condition is selected from the group consisting of fever and pain, and said alginate composition comprises alginate characterized by a molecular weight in a range of from 10 to 75 kDa.

16. The method of claim 12, being for reducing liver damage induced by a hepatotoxic agent, the method comprising administering to a subject in need thereof a therapeutically effective amount of said alginate composition, said administering being effected prior to, concomitant with, or up to 50 minutes after administration of said hepatotoxic agent, thereby treating reducing the liver injury.

17. The method of claim 12, wherein said alginate composition comprises a pharmaceutically acceptable carrier.

18. The method of claim 17, wherein said carrier is an aqueous carrier.

19. The method of claim 18, wherein said alginate composition is characterized by a solution viscosity in a range of from 3 to 50 mPa*seconds, at a shear rate of 1 second$^{-1}$ and at a concentration of 2% (w/v) alginate in said aqueous carrier.

20. The method of claim 17, wherein said alginate composition comprises alginate at a concentration in a range of from 0.4% to 10% (w/v).

21. The method of claim 12, wherein said alginate composition comprises alginate is in a form of a sodium salt.

22. The method of claim 12, wherein administration of said alginate composition comprises co-administration of said alginate composition and said hepatotoxic agent.

23. The method of claim 22, wherein said alginate composition and said hepatotoxic agent are co-formulated within the same composition.

24. The method of claim 15, wherein said alginate composition comprises a pharmaceutically acceptable carrier.

25. The method of claim 15, wherein said alginate composition comprises alginate is in a form of a sodium salt.

26. The method of claim 15, wherein administration of said alginate composition is effected by systemic administration.

27. The method of claim 15, wherein said alginate composition and said hepatotoxic agent are co-formulated within the same composition.

* * * * *